United States Patent
Arimoto et al.

(10) Patent No.: US 11,512,084 B2
(45) Date of Patent: Nov. 29, 2022

(54) DEGRADATION AGENT USING AUTOPHAGIC MECHANISM OF DAMAGED MITOCHONDRIA

(71) Applicant: TOHOKU UNIVERSITY, Miyagi (JP)

(72) Inventors: Hirokazu Arimoto, Miyagi (JP); Kaori Itto, Miyagi (JP); Daiki Takahashi, Miyagi (JP); Jun Moriyama, Miyagi (JP)

(73) Assignee: TOHOKU UNIVERSITY, Miyagi (JP)

( * ) Notice: Subject to any disclaimer, the term of this patent is extended or adjusted under 35 U.S.C. 154(b) by 0 days.

(21) Appl. No.: 16/629,119

(22) PCT Filed: Jul. 9, 2018

(86) PCT No.: PCT/JP2018/025941
§ 371 (c)(1),
(2) Date: Mar. 17, 2020

(87) PCT Pub. No.: WO2019/013181
PCT Pub. Date: Jan. 17, 2019

(65) Prior Publication Data
US 2020/0223848 A1  Jul. 16, 2020

(30) Foreign Application Priority Data
Jul. 10, 2017 (JP) ............................. JP2017-135086

(51) Int. Cl.
| | | |
|---|---|---|
| *A01N 43/90* | (2006.01) | |
| *A61K 31/52* | (2006.01) | |
| *C07D 473/18* | (2006.01) | |
| *C07D 213/56* | (2006.01) | |
| *C07D 519/00* | (2006.01) | |

(52) U.S. Cl.
CPC ......... *C07D 473/18* (2013.01); *C07D 213/56* (2013.01); *C07D 519/00* (2013.01)

(58) Field of Classification Search
CPC ................ C07D 473/18; C07D 213/56; C07D 519/00
USPC ........................................................ 514/263
See application file for complete search history.

(56) References Cited

U.S. PATENT DOCUMENTS

| | | |
|---|---|---|
| 5,625,056 A | 4/1997 | Genieser et al. |
| 2010/0129357 A1 | 5/2010 | Garcia-Martinez et al. |

FOREIGN PATENT DOCUMENTS

| | | |
|---|---|---|
| EP | 0 156 559 | 10/1985 |
| EP | 3 578 549 | 12/2019 |
| JP | 2015-535213 | 12/2015 |
| WO | 2009/063235 | 5/2009 |
| WO | 2012/154975 | 11/2012 |
| WO | 2014/041111 | 3/2014 |
| WO | 2018/143403 | 8/2018 |

OTHER PUBLICATIONS

International Search Report dated Sep. 18, 2018 in International (PCT) Application No. PCT/JP2018/025941.
Ito et al., "Endogenous Nitrated Nucleotide is a Key Mediator of Autophagy and Innate Defense against Bacteria", Molecular Cell, Dec. 26, 2013, vol. 52, pp. 794-804.
Donati et al., "Effects of aging, antiaging calorie restriction and in vivo stimulation of autophagy on the urinary excretion of 8OHdG in male Sprague-Dawley rats", AGE, 2013, vol. 35, pp. 261-270.
Kawazoe et al., "A Mitochondrial Surface-Specific Fluorescent Probe Activated by Bioconversion", Angew. Chem. Int. Ed., 2011, vol. 50, pp. 5478-5481.
Freitas et al., "Descriptor-and Fragment-based QSAR Models for a Series of *Schistosoma mansoni* Purine Nucleoside Inhibitors", J Braz Chem Soc., 2011, vol. 22, No. 9, pp. 1718-1726.
Arimoto et al., "Targeted degradation of cytosolic materials using selective autophagy", Lecture abstracts of conference of The Japan Society for Bioscience, Biotechnology, and Agro chemishy, Mar. 5, 2018, lecture No. 4SY24-5, with English translation & cited in ISR.
Chacinska et al., "Importing Mitochondrial Proteins: Machineries and Mechanisms", Cell, Aug. 21, 2009, vol. 138, pp. 628-644.
Kaizuka et al., "An Autophagic Flux Probe that Releases an Internal Control", Molecular Cell, 2016, vol. 64, pp. 835-849.
Takahashi. "Role of S-guanylation in selective autophagy", Abstract, Master's Thesis of Tohoku University, 2015, with English translation.
Sato et al., "Artificial degradation of proteins using nitroguanine derivatives", Abstract, Master's Thesis of Tohoku University, 2016, with English translation.
Genieser, H., "Preparation of cyclic guanosine-3', 5'-monophosphorothioates as inhibitors and stimulators of cyclic GMP-dependent protein kinase", 1997, pp. 1-2, XP055783258.
Trans et al., "Synthesis of two fluorescent GTP[gamma] S molecules and their biological relevance", Nucleosides, Nucleotides & Nucleic Acids, 2017, vol. 36, No. 6, pp. 379-391.

(Continued)

*Primary Examiner* — Patrick T Lewis
(74) *Attorney, Agent, or Firm* — Wenderoth, Lind & Ponack, LLP

(57) ABSTRACT

Provided is a degrader for injured mitochondria based on an autophagy mechanism, the degrader including a compound or a salt thereof, the compound containing a ligand capable of binding to or accumulating in mitochondria and a substituent represented by the following general formula (1):

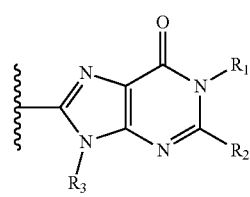

(1)

where $R^1$, $R^2$, and $R^3$ are identical to or different from each other, and each represent a hydrogen atom or the like.

14 Claims, 7 Drawing Sheets

Specification includes a Sequence Listing.

(56) References Cited

OTHER PUBLICATIONS

Babin et al., "Synthèse d'analogues acycliques de C-nucléosides", Journal of Heterocyclic Chemistry, 1983, vol. 20, No. 5, pp. 1169-1173, with English Machine Translation.
Extended European Search Report dated Mar. 23, 2021 in corresponding European Patent Application No. 18831146.8.
Communication pursuant to Article 94(3) EPC issued Mar. 7, 2022 in corresponding European Patent Application No. 18 831 146.8.

Fig.1

Fig.2 pEnGFP-HaloTag-Gap2S SEQUENCE INFORMATION (SEQ ID NO: 1 CONTINUED)

[sequence data illegible]

DEGRADATION AGENT USING AUTOPHAGIC MECHANISM OF DAMAGED MITOCHONDRIA

TECHNICAL FIELD

The present invention relates to degradation of organelles utilizing an autophagy mechanism.

BACKGROUND ART

Mitochondria are organelles essential for cell survival, and are involved in maintenance of calcium homeostasis, regulation of inflammation and cell growth, apoptosis, and the like in addition to an ATP production function.

When the functions of mitochondria are impaired, not only energy production is merely reduced, but the functions exemplified above are impaired. In addition, injured mitochondria excessively produce reactive oxygen species (ROS) to damage cells, to thereby induce cell death. For example, dysfunctions, such as a reduction in mitochondrial membrane potential, are found in Down syndrome, which is a chromosome abnormality, and genetic disorders that are collectively called mitochondrial diseases.

Meanwhile, cells selectively degrade and remove injured mitochondria by an autophagy mechanism (also called mitophagy). However, activity of autophagy is reduced by aging and the like, and hence there exist age-related diseases based on accumulation of injured mitochondria. Examples thereof include Parkinson's disease and cancer.

Under such background, attempts have been made to control mitophagy through the use of compounds, such as pharmaceuticals. Sirolimus (rapamycin) induces autophagy through mTORC1 complex inhibition to promote degradation of mitochondria. However, autophagy caused by sirolimus has poor selectivity for degradation targets, and hence is inefficient because mitochondria are just one of many degradation targets. In addition, there is a problem in that wide-ranging intracellular molecules other than mitochondria are simultaneously degraded, and hence normal physiological functions are affected.

Meanwhile, a group of compounds called uncouplers are also widely used for artificial promotion of mitophagy. The uncoupler is a molecule capable of injuring mitochondrial membranes, and can artificially produce a mitochondrial dysfunction state. Produced dysfunctional mitochondria need to be removed, and hence mitophagy is activated in cells. That is, the uncoupler has the following problem: the uncoupler has an action of further worsening mitochondrial injury due to a disease, and hence is unsuitable for therapeutic use.

CITATION LIST

Non-Patent Literature

NPL 1: "Importing Mitochondrial Proteins: Machineries and Mechanisms", A. Chacinska, C. M. Koehler, D. Milenkovic, T. Lithgow, N. Pfanne, Cell, 138, 628-644 (2009)

NPL 2: Y. Kawazoe, H. Shimogawa, A. Sato, M. Uesugi, Angew. Chem. Int. Ed. 50, 5478-5481 (2011)

NPL 3: Kaizuka et al., Molecular Cell, 64, 835 (2016)

SUMMARY OF INVENTION

Technical Problem

An object to be achieved by the present invention is to provide a novel degrader for mitochondria utilizing an autophagy mechanism.

Solution to Problem

Under such circumstances, the inventors of the present invention have made extensive investigations, and as a result, have found that the above-mentioned object can be achieved by using a compound or a salt thereof, the compound containing a ligand capable of binding to or accumulating in mitochondria and a specific substituent having a specific 1,9-dihydro-6H-purin-6-one ring structure.

Therefore, the present invention provides a degrader, a pharmaceutical, and a compound or a salt thereof as described in the following items:

Item 1. A degrader for injured mitochondria based on an autophagy mechanism, the degrader including a compound or a salt thereof, the compound containing a ligand capable of binding to or accumulating in mitochondria and a substituent represented by the following general formula (1):

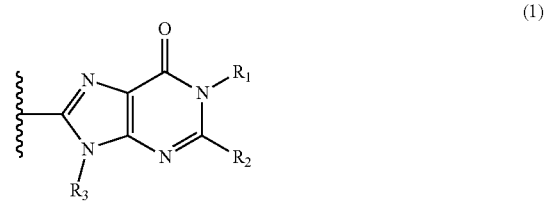

where $R^1$, $R^2$, and $R^3$ are identical to or different from each other, and each represent a hydrogen atom or a substituent, provided that when $R^1$ represents hydrogen and $R^2$ represents an amino group, a case in which $R^3$ represents

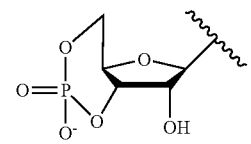

is excluded.

Item 2. A pharmaceutical for preventing or treating a disease that is treatable by degradation of injured mitochondria based on an autophagy mechanism, the pharmaceutical including a compound or a salt thereof, the compound containing a ligand capable of binding to or accumulating in mitochondria and a substituent represented by the following general formula (1):

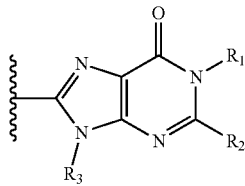

where $R^1$, $R^2$, and $R^3$ are identical to or different from each other, and each represent a hydrogen atom or a substituent, provided that when $R^1$ represents hydrogen and $R^2$ represents an amino group, a case in which $R^3$ represents

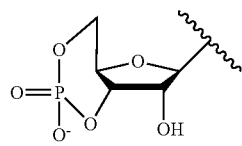

is excluded.

Item 3. The pharmaceutical according to Item 2, wherein the disease that is treatable by degradation of injured mitochondria based on an autophagy mechanism is a neurodegenerative disease, such as Parkinson's disease, Alzheimer's disease, amyotrophic lateral sclerosis (ALS), Huntington's chorea, progressive supranuclear palsy, dementia with Lewy bodies, striatonigral degeneration, olivopontocerebellar atrophy, spinocerebellar degeneration, or Pick's disease, cancer, an inflammatory disease, an age-related disease, a mitochondrial disease (e.g., MELAS, MERRF, chronic progressive external ophthalmoplegia, or Leigh's encephalomyelopathy), a metabolic disease, or Down syndrome.

Item 4. A compound or a salt thereof, the compound including a ligand capable of binding to or accumulating on a mitochondrial surface and a substituent represented by the following general formula (1):

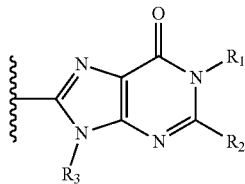

where $R^1$, $R^2$, and $R^3$ are identical to or different from each other, and each represent a hydrogen atom or a substituent, provided that when $R^1$ represents hydrogen and $R^2$ represents an amino group, a case in which $R^3$ represents

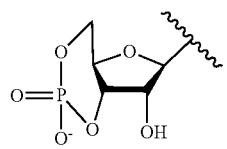

is excluded, the compound or the salt thereof being capable of inducing degradation of injured mitochondria based on an autophagy mechanism.

Item 5. The compound or the salt thereof according to Item 4, wherein the compound or the salt thereof is for use in prevention or treatment of a disease that is treatable by degradation of injured mitochondria based on an autophagy mechanism.

Item 6. A method of preventing or treating a disease that is treatable by degradation of injured mitochondria based on an autophagy mechanism, the method including administering, to a mammal, an effective dose of a compound or a salt thereof, the compound containing a ligand capable of binding to or accumulating in mitochondria and a substituent represented by the following general formula (1):

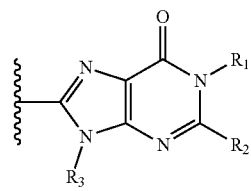

where $R^1$, $R^2$, and $R^3$ are identical to or different from each other, and each represent a hydrogen atom or a substituent, provided that when $R^1$ represents hydrogen and $R^2$ represents an amino group, a case in which $R^3$ represents

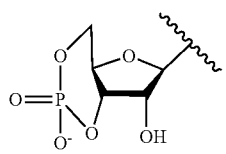

is excluded.

Item 7. A use of a compound or a salt thereof, the compound containing a ligand capable of binding to or accumulating in mitochondria and a substituent represented by the following general formula (1), for producing a preventive or therapeutic agent for a disease that is treatable by degradation of injured mitochondria based on an autophagy mechanism:

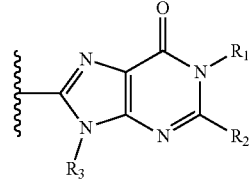

where $R^1$, $R^2$, and $R^3$ are identical to or different from each other, and each represent a hydrogen atom or a substituent, provided that when $R^1$ represents hydrogen and $R^2$ represents an amino group, a case in which $R^3$ represents

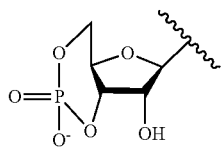
is excluded.
Item 8. The degrader according to Item 1, the pharmaceutical according to Item 2 or 3, the compound or the salt thereof according to Item 4 or 5, the method according to Item 6, or the use according to Item 7, wherein the ligand is a monovalent substituent obtained by removing one hydrogen atom from any one of the following compounds.
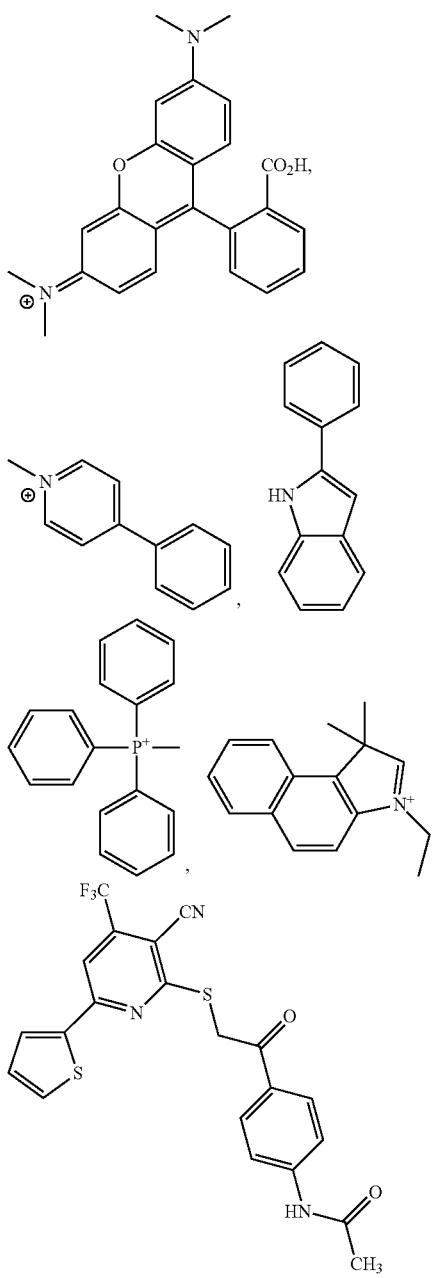
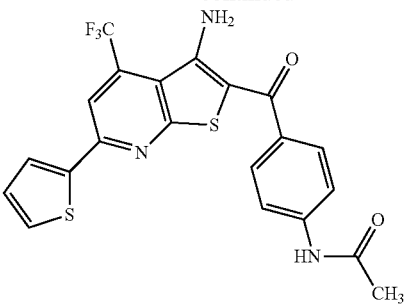
-continued
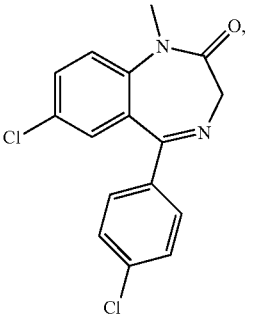
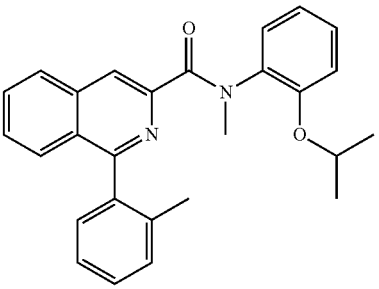
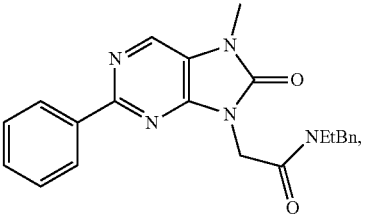
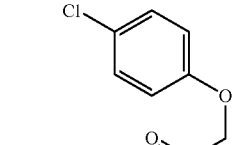
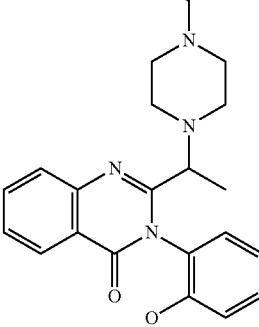

Item 9. The degrader according to Item 1, the pharmaceutical according to Item 2 or 3, the compound or the salt thereof according to Item 4 or 5, the method according to Item 6, the use according to Item 7, or the degrader, the pharmaceutical, the compound or the salt thereof, the method, or the use according to Item 8, wherein the ligand has a structure in which a substituent bonded to a tag molecule is bonded to a protein capable of accumulating in mitochondria, the protein being modified with the tag molecule bonded to the substituent.

Item 10. The degrader according to Item 1, the pharmaceutical according to Item 2 or 3, the compound or the salt thereof according to Item 4 or 5, the method according to Item 6, the use according to Item 7, or the degrader, the pharmaceutical, the compound or the salt thereof, the method, or the use according to Item 8 or 9, wherein the compound containing a ligand capable of binding to or accumulating in mitochondria and a substituent represented by the following general formula (1) is a compound represented by the following general formula (2):

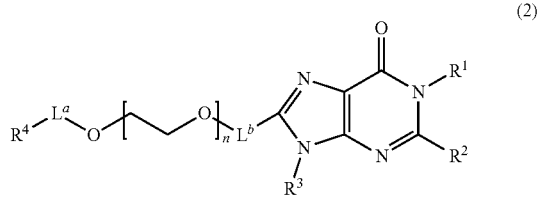

(2)

where:
$R^1$, $R^2$, and $R^3$ are as described above;
$R^4$ represents a ligand capable of binding to or accumulating on a mitochondrial surface;
$L^a$ and $L^b$ are identical to or different from each other, and each represent a bond or a linker; and
"n" represents a natural number of from 1 to 10, provided that when $R^1$ represents hydrogen and $R^2$ represents an amino group, a case in which $R^3$ represents

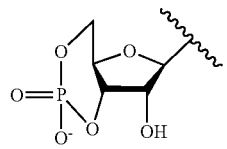

is excluded.

Advantageous Effects of Invention

According to the present invention, the novel degrader for mitochondria based on an autophagy mechanism can be provided.

BRIEF DESCRIPTION OF DRAWINGS

FIG. 1 is an illustration of sequence information on pEmGFP-HaloTag-Omp25.
FIG. 2 is an illustration of sequence information on pEmGFP-HaloTag-Omp25.

DESCRIPTION OF EMBODIMENTS

Figure 3:
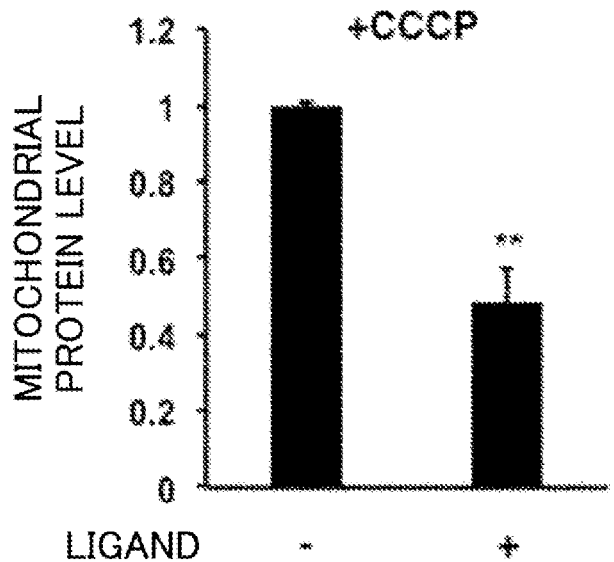
FIG. 3 shows test results of Example 6.

Compound or Salt thereof Capable of Inducing Degradation of Injured Mitochondria Based on Autophagy Mechanism The present invention provides a compound or a salt thereof, the compound containing a ligand capable of binding to or accumulating on a mitochondrial surface and a substituent represented by the following general formula (1):

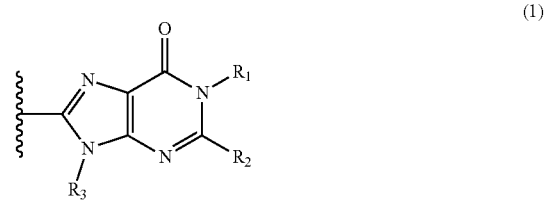

(1)

where $R^1$, $R^2$, and $R^3$ are identical to or different from each other, and each represent a hydrogen atom or a substituent, provided that when $R^1$ represents hydrogen and $R^2$ represents an amino group, a case in which $R^3$ represents

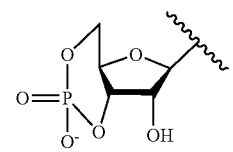

is excluded. In the present invention, the compound containing a ligand capable of binding to or accumulating in mitochondria and a substituent represented by the general formula (1) is sometimes referred to simply as "compound A.".

Hereinafter, substituents have the following meanings, unless otherwise specified.

In the present invention, examples of the "substituent" include a hydrocarbon group that may be substituted, an amino group that may be substituted, a halogen atom, a cyano group, a nitro group, a heterocyclic group that may be substituted, an acyl group, a carbamoyl group that may be substituted, a thiocarbamoyl group that may be substituted, a sulfamoyl group that may be substituted, a hydroxy group that may be substituted, a sulfanyl group that may be substituted, and a silyl group that may be substituted.

Examples of the "hydrocarbon group" include a $C_{1-6}$ alkyl group, a $C_{2-6}$ alkenyl group, a $C_{2-6}$ alkynyl group, a $C_{3-10}$ cycloalkyl group, a $C_{3-10}$ cycloalkenyl group, a $C_{6-14}$ aryl group, and a $C_{7-16}$ aralkyl group.

The "$C_{1-6}$ alkyl group" refers to a linear or branched saturated hydrocarbon group having 1 to 6 carbon atoms. Examples thereof include methyl, ethyl, n-propyl, isopropyl, n-butyl, isobutyl, sec-butyl, tert-butyl, n-pentyl, isopentyl, neopentyl, 1-ethylpropyl, n-hexyl, isohexyl, and 2-ethylbutyl.

The "$C_{2-6}$ alkenyl group" refers to a linear or branched hydrocarbon group having a double bond and having 2 to 6 carbon atoms. Examples thereof include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, and 5-hexenyl.

The "$C_{2-6}$ alkynyl group" refers to a linear or branched hydrocarbon group having a triple bond and having 2 to 6 carbon atoms. Examples thereof include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, and 4-methyl-2-pentynyl.

The "$C_{3-10}$ cycloalkyl group" refers to a cyclic alkyl group having 3 to 10 carbon atoms. Examples thereof include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, and adamantyl.

The "$C_{3-10}$ cycloalkenyl group" refers to a cyclic hydrocarbon group having a double bond and having 3 to 10 carbon atoms. Examples thereof include cyclopropenyl, cyclobutenyl, cyclopentenyl, cyclohexenyl, cycloheptenyl, and cyclooctenyl.

Examples of the "$C_{6-14}$ aryl group" include phenyl, 1-naphthyl, 2-naphthyl, 1-anthryl, 2-anthryl, and 9-anthryl.

Examples of the "$C_{7-16}$ aralkyl group" include benzyl, phenethyl, naphthylmethyl, and phenylpropyl.

Examples of the substituent in each of the "hydrocarbon group that may be substituted", the "amino group that may be substituted", the "heterocyclic group that may be substituted", the "carbamoyl group that may be substituted", the "thiocarbamoyl group that may be substituted", the "sulfamoyl group that may be substituted", the "hydroxy group that may be substituted", the "sulfanyl group that may be substituted", and the "silyl group that may be substituted" include: an amino group that may be substituted with a hydrocarbon group; a halogen atom; a cyano group; a nitro group; a heterocyclic group that may be substituted with a hydrocarbon group; an acyl group; a carbamoyl group that may be substituted with a hydrocarbon group; a thiocarbamoyl group that may be substituted with a hydrocarbon group; a sulfamoyl group; a hydroxy group that may be substituted with a hydrocarbon group; a sulfanyl group that may be substituted with a hydrocarbon group; and a silyl group that may be substituted with a hydrocarbon group. When the "hydrocarbon group that may be substituted", the "amino group that may be substituted", the "heterocyclic group that may be substituted", the "carbamoyl group that may be substituted", the "thiocarbamoyl group that may be substituted", the "sulfamoyl group that may be substituted", the "hydroxy group that may be substituted", the "sulfanyl group that may be substituted", or the "silyl group that may be substituted" has a substituent, the number of substituents is not particularly limited, but may be appropriately set to, for example, from 1 to 5, from 1 to 3, or 1.

Examples of the "halogen atom" include fluorine, chlorine, bromine, and iodine.

An example of the "heterocyclic group" is a seven- to ten-membered saturated or unsaturated heterocyclic group containing 1 to 4 heteroatoms each selected from the group consisting of a nitrogen atom, a sulfur atom, and an oxygen atom. More specific examples thereof include a thienyl group, a thiazolyl group, a furyl group, a piperidinyl group, a piperazinyl group, a pyridinyl group, a pyrrolinyl group, a morpholinyl group, an imidazolyl group, an indolyl group, a pyrimidinyl group, an oxazolyl group, a pyrrolidinyl group, an indolizinyl group, and a benzofuranyl group.

Examples of the "acyl group" include a formyl group, and an alkylcarbonyl group in which an alkyl moiety is the above-mentioned $C_{1-6}$ alkyl group.

In the present invention, $R^1$ represents preferably a hydrogen atom, a hydrocarbon group, or the like, more preferably a hydrogen atom, a $C_{1-6}$ (preferably $C_{1-3}$) alkyl group, or the like, still more preferably a hydrogen atom.

In the present invention, $R^2$ represents preferably a hydrogen atom, a hydrocarbon group that may be substituted (preferably a hydrocarbon group that may be substituted with at least one kind selected from the group consisting of an amino group and a carbamoyl group, more preferably a $C_{1-6}$ alkyl group that may be substituted with at least one kind selected from the group consisting of an amino group and a carbamoyl group), an amino group that may be substituted, a carbamoyl group that may be substituted, or the like; more preferably a substituted hydrocarbon group (preferably a hydrocarbon group substituted with at least one kind selected from the group consisting of an amino group and a carbamoyl group, more preferably a $C_{1-6}$ alkyl group substituted with at least one kind selected from the group consisting of an amino group and a carbamoyl group), an amino group, a carbamoyl group, or the like; still more preferably a hydrocarbon group substituted with an amino group (preferably a $C_{1-6}$ alkyl group substituted with an amino group) group, an amino group, or the like.

In the present invention, $R^3$ is not particularly limited, but for example, represents preferably a hydrogen atom, a hydrocarbon group that may be substituted, or the like; more preferably a hydrogen atom, or a hydrocarbon (e.g., a $C_{6-14}$ aryl group or a $C_{7-16}$ aralkyl group) that may be substituted with a halogen; still more preferably a hydrocarbon (a $C_{6-14}$ aryl group (preferably phenyl or naphthyl, more preferably phenyl) or a $C_{7-16}$ aralkyl group (preferably a $C_{7-12}$ phenylalkyl or a $C_{11}$-17 naphthylalkyl, more preferably a $C_{7-12}$ phenylalkyl) substituted with a halogen (preferably fluorine)

The "ligand capable of binding to or accumulating in mitochondria" means a ligand capable of binding to mitochondria by covalent bonding, hydrogen bonding, or the like or accumulating in mitochondria (in the inside of mitochondria or on the surface thereof). As such ligand, ligands known in the technical field to which the present invention belongs may be widely used. For example, many compounds capable of accumulating in mitochondria are known, and examples thereof include low-molecular-weight ligands capable of binding to proteins on the mitochondrial outer membrane, such as 8 kDa translocator protein (TSPO) and voltage-dependent anion channel (VDAC). In addition, as typified by Rhodamine dyes and triphenylphosphonium salts, it is also known that positively charged compounds accumulate in mitochondria. Also in Y. Kawazoe, H. Shimogawa, A. Sato, M. Uesugi, Angew. Chem. Int. Ed. 50, 5478-5481 (2011), there is a description of molecules that accumulate on the mitochondrial surface.

Examples of the ligand include a monovalent substituent obtained by removing one hydrogen atom from any one of the following compounds:

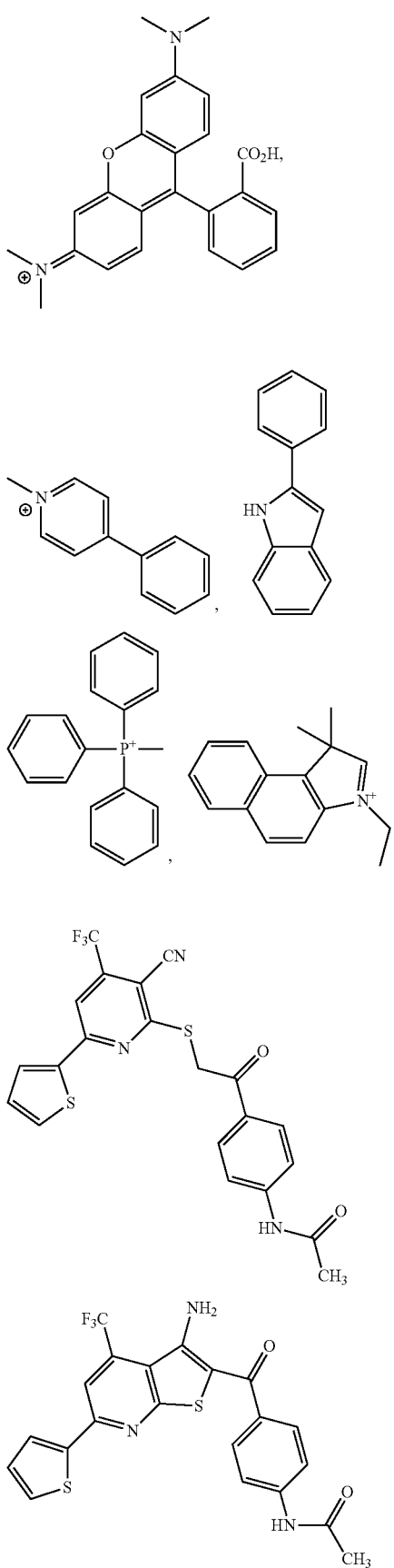

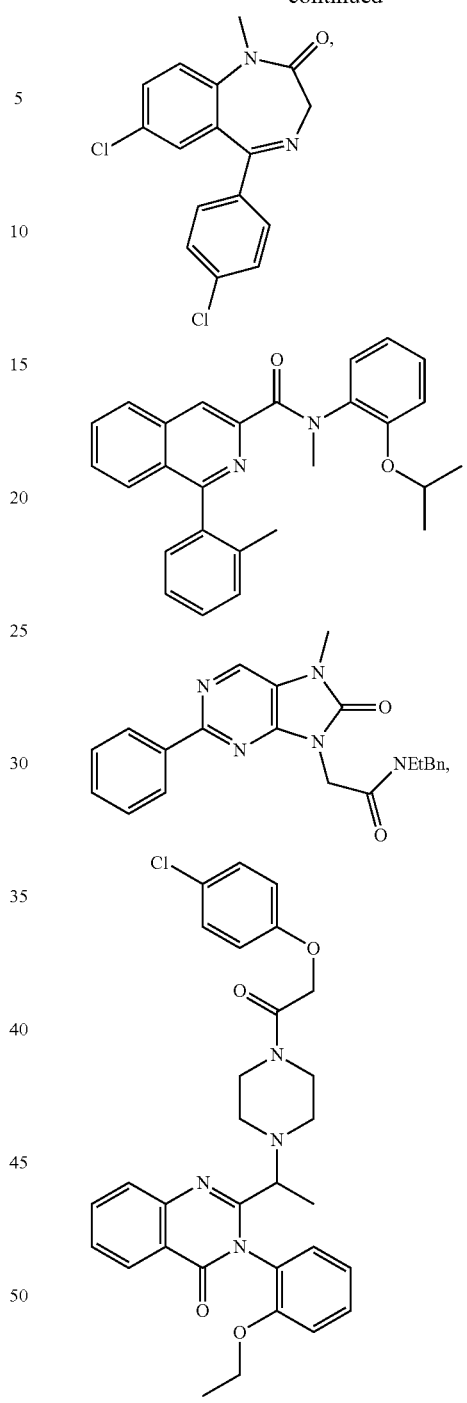

In addition, in a preferred embodiment of the present invention, in addition to the foregoing, examples of the ligand also include a monovalent group obtained by removing one hydrogen atom from a compound represented by the following formula, the group having a structure in which 1 to 5 (e.g., 1 to 3, 1 to 2, or 1) hydrogen atoms in a phenyl group in the formula are each substituted with a substituent (e.g., at least one kind of group selected from the group consisting of a linear or branched C1 to C6 alkyl group, a halogen, and a linear or branched C1 to C6 alkoxy group).

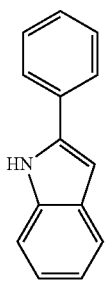

In the present invention, examples of the halogen include fluorine, chlorine, bromine, and iodine. In addition, in a preferred embodiment of the present invention, examples of the monovalent group obtained by removing one hydrogen atom from any one of the compounds given above as the ligand may include the following.

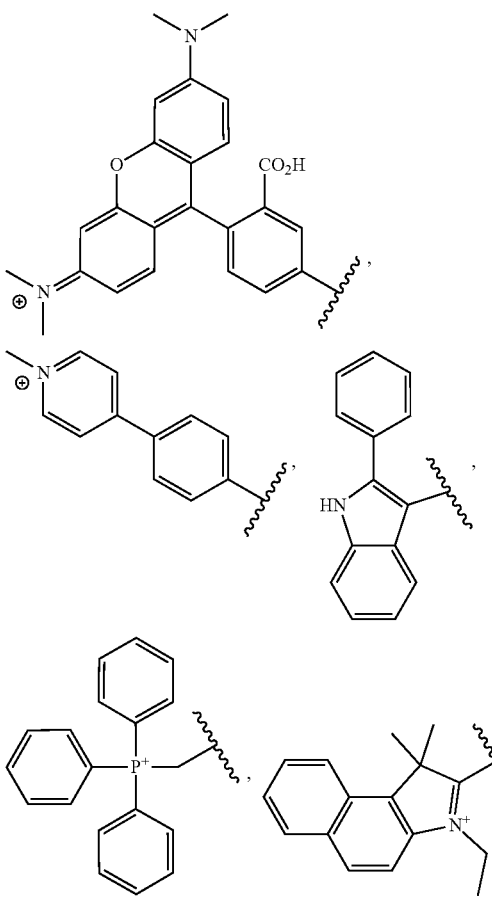

In addition, examples of the ligand also include, in addition to the foregoing, a substituent having a structure in which, in the following formula, 1 to 5 (e.g., 1 to 3, 1 to 2, or 1) hydrogen atoms in a phenyl group in the formula are each substituted with a substituent (e.g., at least one group selected from the group consisting of a linear or branched C1 to C6 alkyl group, a halogen, and a linear or branched C1 to C6 alkoxy group).

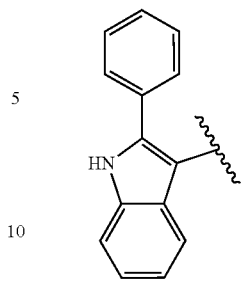

In addition, as the ligand, a protein capable of accumulating in the inside of mitochondria or on the surface thereof may also be utilized. An example of such protein is a protein having added thereto a signal sequence (mitochondrial targeting sequence). As the mitochondrial targeting signal sequence, sequences known in the technical field to which the present invention belongs may be widely used (e.g., "Importing Mitochondrial Proteins: Machineries and Mechanisms", A. Chacinska, C. M. Koehler, D. Milenkovic, T. Lithgow, N. Pfanne, Cell, 138, 628-644 (2009)). When such protein is used as the ligand, a tag technology may be used in order to bond the ligand to the substituent represented by the general formula (1). Specifically, as the protein capable of accumulating in the inside of mitochondria or on the surface thereof, there may be used a fusion protein obtained by combining a tag protein and the mitochondrial targeting signal sequence. Examples of the tag protein include HaloTag (HT), SNAP-tag, CLIP-tag, and Ash-tag (assembly helper tag). Such fusion protein may be, for example, a fusion protein obtained by further fusing a fluorescent protein (e.g., EmGFP).

In such embodiment, an example of the ligand may be a ligand having a structure in which a substituent (e.g., in the case of using HaloTag, a halogen atom, or a hydrocarbon group substituted with a halogen atom) bonded to a tag molecule is bonded to a protein capable of accumulating in mitochondria, the protein being modified with the tag molecule bonded to the substituent.

In addition, in a typical embodiment of the present invention, an example of the compound containing a ligand capable of binding to or accumulating in mitochondria and a substituent represented by the following general formula (1) may be a compound represented by the following general formula (2) or a salt thereof:

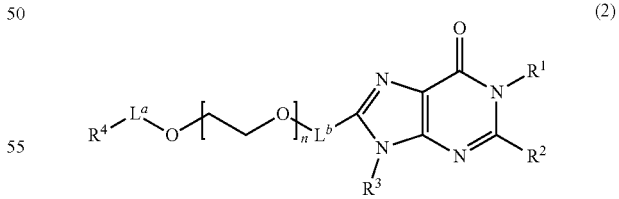

(2)

where:
$R^1$, $R^2$, and $R^3$ are as described above;
$R^4$ represents a ligand capable of binding to or accumulating on a mitochondrial surface;
$L^a$ and $L^b$ are identical to or different from each other, and each represent a bond or a linker; and
"n" represents a natural number of from 1 to 10, provided that when $R^1$ represents hydrogen and $R^2$ represents an amino group, a case in which $R^3$ represents

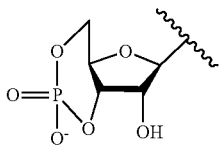

is excluded.

Herein, the compound represented by the general formula (2) is sometimes referred to simply as "compound A'".

In such embodiment, the -$L^a$—O—(—CH$_2$—CH$_2$—O—)$_n$-$L^b$- moiety serves as a linker for linking the ligand capable of binding to or accumulating in mitochondria and the substituent represented by the general formula (1).

When $L^a$ represents a linker, an example of such linker is a chain linker whose main chain is formed of 1 to 15 atoms, preferably 1 to 10 atoms. An example of such chain linker may be a chain linker formed of at least one kind selected from the group consisting of —CH$_2$—, —CH$_2$=CH$_2$—, —C≡C—, —C(=O)—, —NH—, —O—, —S—, —CH=N—, —N=CH—, —C(=S)—, and —C(=NH)— (Therefore, for example, one selected from the above-mentioned group may be used as the linker, or a combination of two or more (which may be of one kind or may be of two or more kinds) selected from the above-mentioned group may be used as the linker.). In addition, such linker preferably contains at least one kind of structure selected from the group consisting of an amide bond [—C(=O)—NH— or —NH—C(=O)—], an ether bond (—O—), a thioether bond (—S—), an ester bond [—C(=O)—O— or —O—C(=O)—], and a urethane bond [—NH—C(=O)— or —C(=O=)—NH—].

In addition, such linker may contain, in its main chain, one or two (preferably one) divalent cyclic structure(s) (e.g., a five-membered or six-membered unsaturated hydrocarbon ring group; or a five-membered or six-membered heterocyclic group having (preferably one to four, more preferably one to three of) at least one kind of heteroatom selected from the group consisting of nitrogen, oxygen, and sulfur).

As the five-membered or six-membered divalent unsaturated hydrocarbon ring group, for example,

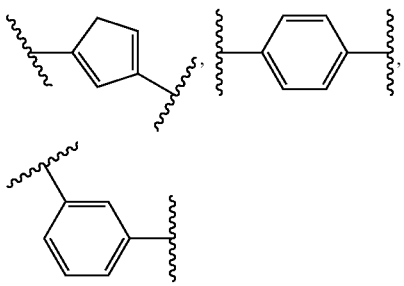

and the like are given, and a phenylene group and the like are preferably given.

Examples of the five-membered or six-membered divalent heterocycle having (preferably one to four, more preferably two or three of) at least one kind of heteroatom selected from the group consisting of nitrogen, oxygen, and sulfur include divalent groups each obtained by removing two hydrogen atoms from pyrrole, pyrrolidine, pyrazole, triazole, pyridine, furan, pyran, thiophene, morpholine, or the like. Of those heterocycles, five-membered or six-membered divalent heterocyclic groups each having 1 to 3 (preferably 2 or 3) nitrogen atoms as the heteroatoms (e.g., divalent groups each obtained by removing two hydrogen atoms from a pyrazole ring or a triazole ring, more specifically, for example,

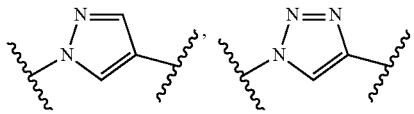 [SMILES: *c1cnn(*)c1 ; *c1cn(*)nn1]

and the like) are given.

Of those divalent cyclic structures, preferred examples include divalent aromatic rings (including an aromatic hydrocarbon ring group and an aromatic heterocyclic group). As such divalent aromatic rings, divalent groups each obtained by removing two hydrogen atoms from a five- or six-membered ring, such as furan, pyrrole, or benzene, and the like may be given, and more specifically, for example,

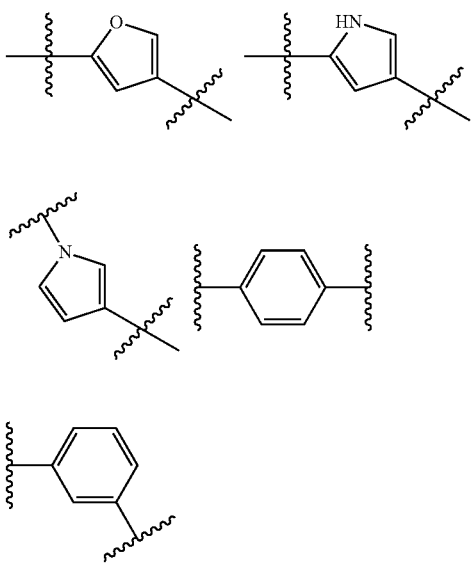 [SMILES: *c1coc(*)c1 ; *c1c[nH]c(*)c1 ; *c1ccn(*)c1 ; *c1ccc(*)cc1 ; *c1cccc(*)c1]

and the like are given.

Such chain linker may be substituted with a substituent, and may be preferably substituted with, for example, at least one kind selected from the group consisting of a halogen, a hydroxy group, and a C$_{1-6}$ alkyl group. When such chain linker is substituted, the number of substituents is not particularly limited, but may be appropriately designed within the range of, for example, from 1 to 3, from 1 to 2, or 1.

In the present invention, the expression "whose main chain is formed of 1 to 10 atoms" means that the number of atoms forming the main chain excluding hydrogen atoms is from 1 to 0.

Therefore, a case in which $L^a$ represents the following structure:

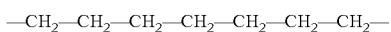

may be expressed as a chain linker whose main chain is formed of 7 atoms.

In addition, a case in which $L^a$ represents the following structure:

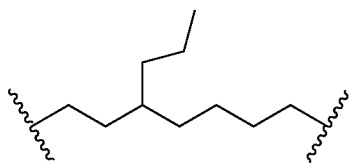 [SMILES: *CCCCC(CC*)CCC]

may also be expressed as a chain linker whose main chain is formed of 7 atoms.

In addition, a case in which $L^a$ represents the following structure:

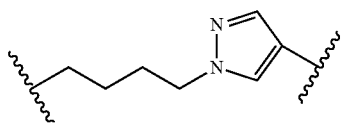 [SMILES: *CCCCn1cc(*)cn1]

may be expressed as a chain linker whose main chain is formed of 9 atoms.

When $L^b$ represents a linker, an example of such linker is a chain linker whose main chain is formed of 1 to 15 atoms, preferably 1 to 10 atoms. An example of such chain linker may be a chain linker formed of at least one kind selected from the group consisting of —CH$_2$—, —CH$_2$=CH$_2$—, —C≡C—, —C(=O)—, —NH—, —O—, —S—, —CH=N—, —N=CH—, —C(=S)—, and —C(=NH)— (Therefore, for example, one selected from the above-mentioned group may be used as the linker, or a combination of two or more (which may be of one kind or may be of two or more kinds) selected from the above-mentioned group may be used as the linker.). Such linker preferably contains at least one kind of structure selected from the group consisting of an amide bond [—C(=O)—NH— or —NH—C(=O)—], an ether bond (—O—), a thioether bond (—S—), an ester bond [—C(=O)—O— or —O—C(=O)—], and a urethane bond [—NH—C(=O)— or —C(=O=)—NH—]. Any such linker may be substituted with a substituent, and may be preferably substituted with, for example, at least one kind selected from the group consisting of a halogen, a hydroxy group, a C$_{1-6}$ alkyl group, and an amino group that may have, as a substituent, an alkyl group and/or an acyl group. When such chain linker is substituted, the number of substituents is not particularly limited, but may be appropriately designed within the range of, for example, from 1 to 3, from 1 to 2, or 1.

Also when $L^b$ represents a linker, the linker may contain, in its main chain, one or two (preferably one) divalent cyclic structure(s) (e.g., a five-membered or six-membered unsaturated hydrocarbon ring group; or a five-membered or six-membered heterocyclic group having (preferably one to four, more preferably one to three of) at least one kind of heteroatom selected from the group consisting of nitrogen, oxygen, and sulfur). Examples of the five-membered or six-membered unsaturated hydrocarbon ring group; the five-membered or six-membered heterocyclic group having at least one kind of heteroatom selected from the group consisting of nitrogen, oxygen, and sulfur, and the like include those described above for $L^a$. In addition, also in $L^b$, preferred examples of the divalent cyclic structure include divalent aromatic rings (including an aromatic hydrocarbon ring group and an aromatic heterocyclic group), and more specifically, may include divalent groups each obtained by removing two hydrogen atoms from a five- or six-membered ring, such as furan, pyrrole, or benzene, and the like. Still more specifically, for example,

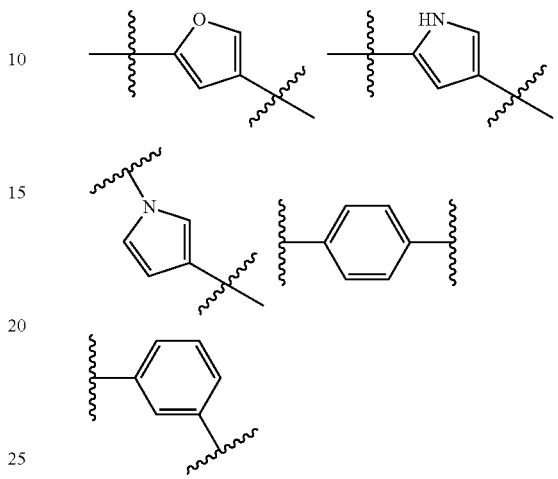

and the like are given.

Symbol "n" represents a natural number of from 1 to 10, preferably from 1 to 8, more preferably from 1 to 6, still more preferably from 1 to 5.

The compound according to the present invention is produced, for example, as shown in the following reaction formula-1:

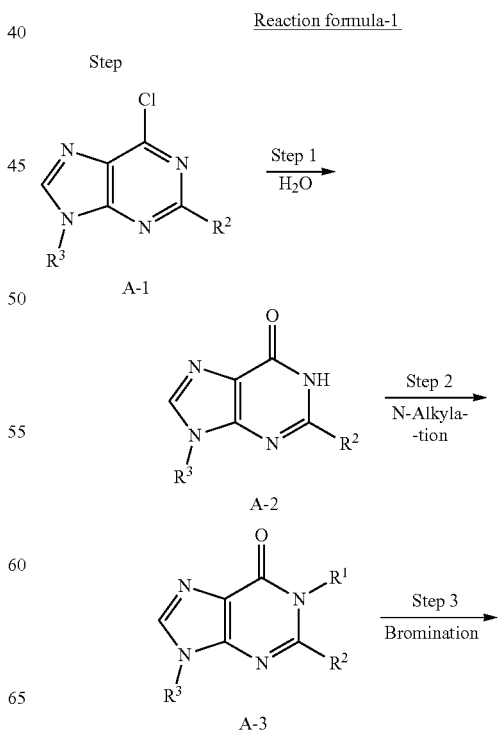

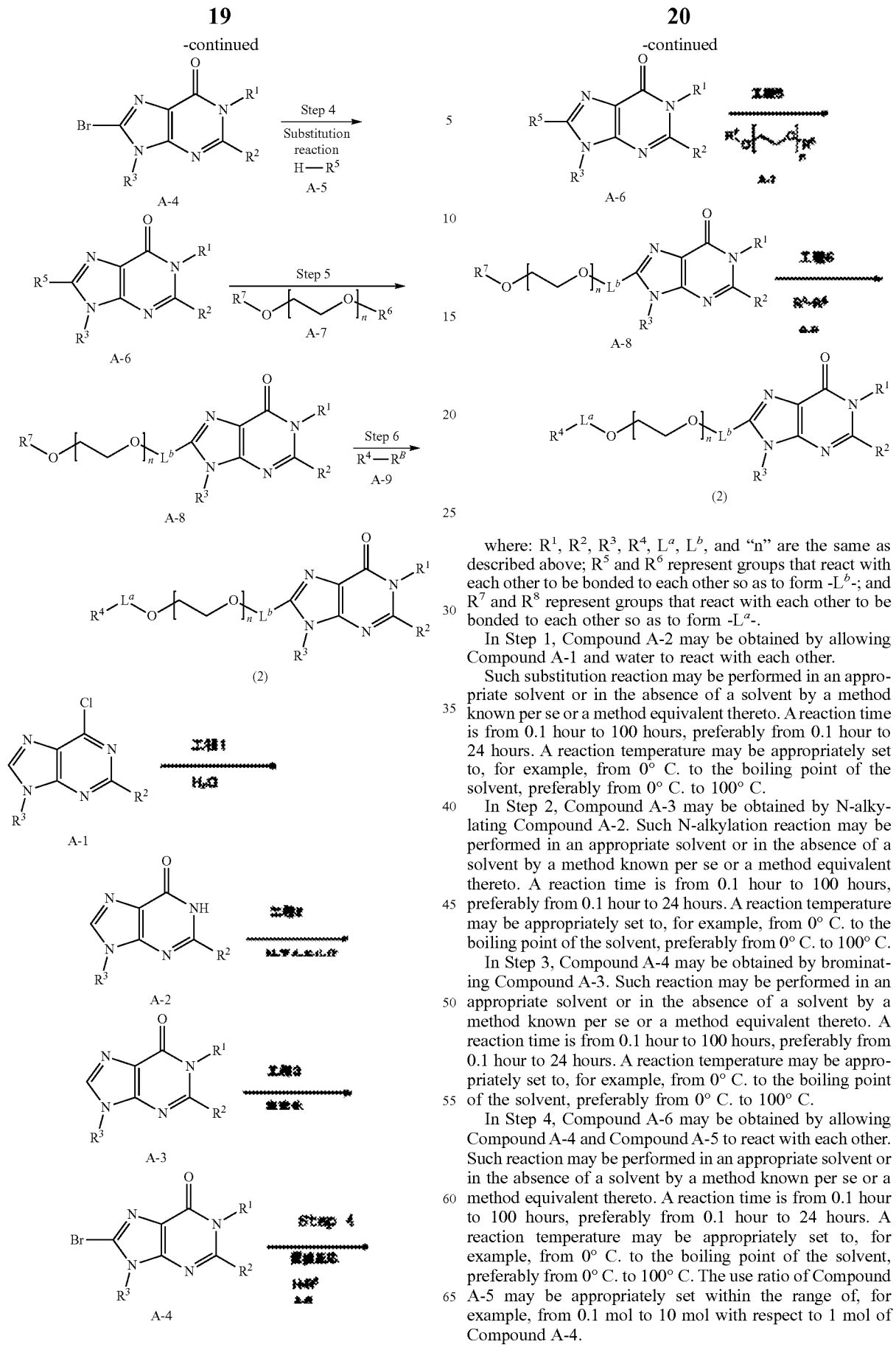

where: $R^1$, $R^2$, $R^3$, $R^4$, $L^a$, $L^b$, and "n" are the same as described above; $R^5$ and $R^6$ represent groups that react with each other to be bonded to each other so as to form $-L^b-$; and $R^7$ and $R^8$ represent groups that react with each other to be bonded to each other so as to form $-L^a-$.

In Step 1, Compound A-2 may be obtained by allowing Compound A-1 and water to react with each other.

Such substitution reaction may be performed in an appropriate solvent or in the absence of a solvent by a method known per se or a method equivalent thereto. A reaction time is from 0.1 hour to 100 hours, preferably from 0.1 hour to 24 hours. A reaction temperature may be appropriately set to, for example, from 0° C. to the boiling point of the solvent, preferably from 0° C. to 100° C.

In Step 2, Compound A-3 may be obtained by N-alkylating Compound A-2. Such N-alkylation reaction may be performed in an appropriate solvent or in the absence of a solvent by a method known per se or a method equivalent thereto. A reaction time is from 0.1 hour to 100 hours, preferably from 0.1 hour to 24 hours. A reaction temperature may be appropriately set to, for example, from 0° C. to the boiling point of the solvent, preferably from 0° C. to 100° C.

In Step 3, Compound A-4 may be obtained by brominating Compound A-3. Such reaction may be performed in an appropriate solvent or in the absence of a solvent by a method known per se or a method equivalent thereto. A reaction time is from 0.1 hour to 100 hours, preferably from 0.1 hour to 24 hours. A reaction temperature may be appropriately set to, for example, from 0° C. to the boiling point of the solvent, preferably from 0° C. to 100° C.

In Step 4, Compound A-6 may be obtained by allowing Compound A-4 and Compound A-5 to react with each other. Such reaction may be performed in an appropriate solvent or in the absence of a solvent by a method known per se or a method equivalent thereto. A reaction time is from 0.1 hour to 100 hours, preferably from 0.1 hour to 24 hours. A reaction temperature may be appropriately set to, for example, from 0° C. to the boiling point of the solvent, preferably from 0° C. to 100° C. The use ratio of Compound A-5 may be appropriately set within the range of, for example, from 0.1 mol to 10 mol with respect to 1 mol of Compound A-4.

In Step 5, Compound A-8 may be obtained by allowing Compound A-6 and Compound A-7 to react with each other. Such reaction may be performed in an appropriate solvent or in the absence of a solvent by a method known per se or a method equivalent thereto. A reaction time is from 0.1 hour to 100 hours, preferably from 0.1 hour to 24 hours. A reaction temperature may be appropriately set to, for example, from 0° C. to the boiling point of the solvent, preferably from 0° C. to 100° C. The use ratio of Compound A-7 may be appropriately set within the range of, for example, from 0.1 mol to 10 mol with respect to 1 mol of Compound A-6.

In Step 6, the compound A' may be obtained by allowing Compound A-8 and Compound A-9 to react with each other. Such reaction may be performed in an appropriate solvent or in the absence of a solvent by a method known per se or a method equivalent thereto. A reaction time is from 0.1 hour to 100 hours, preferably from 0.1 hour to 24 hours. A reaction temperature may be appropriately set to, for example, from 0° C. to the boiling point of the solvent, preferably from 0° C. to 100° C. The use ratio of Compound A-9 may be appropriately set within the range of, for example, from 0.1 mol to 10 mol with respect to 1 mol of Compound A-8.

In addition, the compound according to the present invention may also be produced as shown in the following reaction formula II:

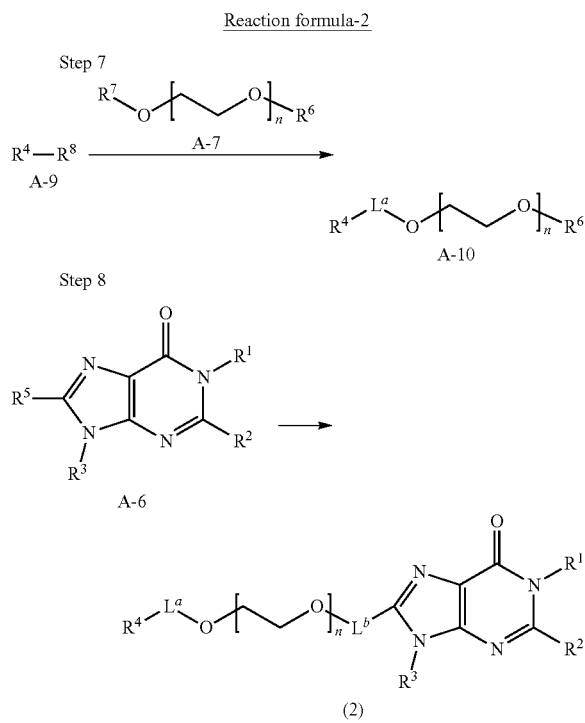

where $R^1$, $R^2$, $R^3$, $R^4$, $R^5$, $R^6$, $R^7$, $R^8$, $L^a$, $L^b$, and "n" are the same as described above.

In Step 7, Compound A-10 may be obtained by allowing Compound A-9 and Compound A-7 to react with each other. Such reaction may be performed in an appropriate solvent or in the absence of a solvent by a method known per se or a method equivalent thereto. A reaction time is from 0.1 hour to 100 hours, preferably from 0.1 hour to 24 hours. A reaction temperature may be appropriately set to, for example, from 0° C. to the boiling point of the solvent, preferably from 0° C. to 100° C. The use ratio of Compound A-7 may be appropriately set within the range of, for example, from 0.1 mol to 10 mol with respect to 1 mol of Compound A-9.

In Step 8, the compound A' may be obtained by allowing Compound A-10 and Compound A-6 to react with each other. Such reaction may be performed in an appropriate solvent or in the absence of a solvent by a method known per se or a method equivalent thereto. A reaction time is from 0.1 hour to 100 hours, preferably from 0.1 hour to 24 hours. A reaction temperature may be appropriately set to, for example, from 0° C. to the boiling point of the solvent, preferably from 0° C. to 100° C. The use ratio of Compound A-6 may be appropriately set within the range of, for example, from 0.1 mol to 10 mol with respect to 1 mol of Compound A-10.

Each of the compounds obtained in the respective steps of the above-mentioned production method may be subjected to the next step after having been isolated/purified by known separating/purifying means, such as concentration, reduced-pressure concentration, crystallization, solvent extraction, reprecipitation, or chromatography, or without being isolated/purified.

In the present invention, the salt of the compound A encompasses an acid addition salt and a salt with a base. Specific examples of the acid addition salt include: inorganic acid salts, such as a hydrochloride, a hydrobromide, a hydroiodide, a sulfate, a perchlorate, and a phosphate; organic acid salts, such as an oxalate, a malonate, a succinate, a maleate, a fumarate, a lactate, a malate, a citrate, a tartrate, a benzoate, a trifluoroacetate, an acetate, a methanesulfonate, a p-toluenesulfonate, and a trifluoromethanesulfonate; and acidic amino acid salts, such as a glutamate and an aspartate. Specific examples of the salt with a base include: alkali metal or alkaline earth metal salts, such as a sodium salt, a potassium salt, and a calcium salt; salts with organic bases, such as a pyridine salt and a triethylamine salt; and salts with basic amino acids, such as lysine and arginine. In addition, when the compound A is a cation, the salt of the compound A also encompasses a halide (e.g., a chloride) and the like.

In addition, in the present invention, when the compound A or the salt thereof has an isomer, such as an optical isomer, a stereoisomer, or a regioisomer, the present invention may encompass both of an invention using any of the isomers and an invention using a mixture of a variety of isomers, unless it is clearly specified which of the isomers is used.

In the present invention, the compound A may be present in the form of a hydrate or a solvate, and hence the compound of the present invention also encompasses such hydrate and solvate.

A solvent forming the solvate is exemplified by alcohols, such as ethanol and propanol, organic acids, such as acetic acid, esters, such as ethyl acetate, ethers, such as tetrahydrofuran and diethyl ether, ketones, such as acetone, and DMSO.

Pharmaceutical

The compound A or the salt thereof of the present invention is capable of inducing degradation of injured mitochondria by an autophagy mechanism. Accordingly, the present invention provides a pharmaceutical for preventing or treating a disease that is treatable by degradation of injured mitochondria, the pharmaceutical including the compound A or the salt thereof.

Examples of the disease that is treatable by degradation of injured mitochondria include a neurodegenerative disease, such as Parkinson's disease, Alzheimer's disease, amyotrophic lateral sclerosis (ALS), Huntington's chorea, progressive supranuclear palsy, dementia with Lewy bodies, striatonigral degeneration, olivopontocerebellar atrophy, spinocerebellar degeneration, or Pick's disease, cancer, an inflammatory disease, an age-related disease, a metabolic disease, a mitochondrial disease (e.g., MELAS, MERRF, chronic progressive external ophthalmoplegia, or Leigh's encephalomyelopathy), and Down syndrome.

In the present invention, the compound A or the salt thereof serving as the active ingredient of the present invention may be used alone as a pharmaceutical, or may be used as a pharmaceutical composition in combination with any of various pharmaceutically acceptable carriers (e.g., a tonicity agent, a chelating agent, a stabilizing agent, a pH regulator, a preservative, an antioxidant, a solubilizing agent, or a thickening agent).

Examples of the tonicity agent include: sugars, such as glucose, trehalose, lactose, fructose, mannitol, xylitol, and sorbitol; polyhydric alcohols, such as glycerol, polyethylene glycol, and propylene glycol; and inorganic salts, such as sodium chloride, potassium chloride, and calcium chloride. Those tonicity agents may be used alone or in combination thereof.

Examples of the chelating agent include: edetates, such as disodium edetate, calcium disodium edetate, trisodium edetate, tetrasodium edetate, and calcium edetate; ethylenediaminetetraacetates; nitrilotriacetic acid or salts thereof; sodium hexametaphosphate; and citric acid. Those chelating agents may be used alone or in combination thereof.

An example of the stabilizing agent is sodium hydrogen sulfite.

Examples of the pH regulator include acids, such as hydrochloric acid, carbonic acid, acetic acid, and citric acid, and also include: alkali metal hydroxides, such as sodium hydroxide and potassium hydroxide; alkali metal carbonates or hydrogen carbonates, such as sodium carbonate; alkali metal acetates, such as sodium acetate; alkali metal citrates, such as sodium citrate; and bases, such as trometamol. Those pH regulators may be used alone or in combination thereof.

Examples of the preservative include: sorbic acid; potassium sorbate; parahydroxybenzoates, such as methyl parahydroxybenzoate, ethyl parahydroxybenzoate, propyl parahydroxybenzoate, and butyl parahydroxybenzoate; quaternary ammonium salts, such as chlorhexidine gluconate, benzalkonium chloride, benzethonium chloride, and cetylpyridinium chloride; alkylpolyaminoethylglycine; chlorobutanol; polyquad; polyhexamethylene biguanide; and chlorhexidine. Those preservatives may be used alone or in combination thereof.

Examples of the antioxidant include sodium hydrogen sulfite, dried sodium sulfite, sodium pyrosulfite, and concentrated mixed tocopherols. Those antioxidants may be used alone or in combination thereof.

Examples of the solubilizing agent include sodium benzoate, glycerol, D-sorbitol, glucose, propylene glycol, hydroxypropyl methylcellulose, polyvinylpyrrolidone, macrogol, and D-mannitol. Those solubilizing agents may be used alone or in combination thereof.

Examples of the thickening agent include polyethylene glycol, methyl cellulose, ethyl cellulose, carmellose sodium, xanthan gum, sodium chondroitin sulfate, hydroxyethyl cellulose, hydroxypropyl cellulose, hydroxypropyl methylcellulose, polyvinylpyrrolidone, and polyvinyl alcohol. Those thickening agents may be used alone or in combination thereof.

In addition, the pharmaceutical composition may further contain, in addition to the compound A or the salt thereof, a compound known to have a preventive or therapeutic action on the disease that is treatable by degradation of injured mitochondria. In addition, the pharmaceutical composition may further contain, in addition to the compound A or the salt thereof, a compound known or suggested to have an autophagy-inducing action. An example of such compound is sirolimus (rapamycin). In addition, another example of such compound is the compound described in Kaizuka et al., Molecular Cell, 64, 835 (2016). Those compounds may be used alone or in combination thereof.

In the embodiment of the pharmaceutical composition, the content of the compound A or the salt thereof in the composition is not particularly limited, and may be appropriately set within, for example, conditions such as 90 mass % or more, 70 mass % or more, 50 mass % or more, 30 mass % or more, 10 mass % or more, 5 mass % or more, and 1 mass % or more in terms of the content of the compound A.

A dosage form is not particularly limited, and examples thereof may include various dosage forms including: orally administered agents, such as a tablet, a pill, a capsule, a powder, a granule, and a syrup; and parenterally administered agents, such as an injection (e.g., intravenous injection, intramuscular injection, or local injection), a gargle, a drop, external preparations (an ointment, a cream, a patch, and an inhalant), and a suppository. Of the dosage forms, for example, orally administered agents (e.g., a tablet, a pill, a capsule, a powder, a granule, and a syrup) and external preparations (an ointment, a cream, a patch, and an inhalant) are preferred.

In the present invention, the dose of the compound A or the salt thereof varies depending on, for example, an administration route and the age, body weight, or symptom of a patient, and hence cannot be uniquely defined. However, the dose only needs to be such an amount that a daily dose for adults is generally about 5,000 mg or less, preferably about 1,000 mg or less, more preferably 500 mg or less in terms of the dose of the compound A. The lower limit of the dose of the compound A or the salt thereof is also not particularly limited, and may be appropriately set within, for example, such a range that a daily dose for adults is generally 1 mg or more, preferably 10 mg or more, more preferably 100 mg or more in terms of the dose of the compound A. When administered once daily, the compound A or the salt thereof only needs to be contained in the above-mentioned amount in a single dose. When administered three times daily, the compound A or the salt thereof only needs to be contained in an amount corresponding to one-third of the above-mentioned amount in a single dose.

The pharmaceutical of the present invention is administered to patients, such as mammals. Examples of the mammals include humans, monkeys, mice, rats, rabbits, cats, dogs, pigs, cattle, horses, and sheep.

Degrader for Injured Mitochondria

The present invention also provides a degrader for injured mitochondria based on an autophagy mechanism, the degrader including the compound A or the salt thereof. The active ingredient, dosage form, dose, and the like of the degrader are the same as those described above for the pharmaceutical of the present invention.

EXAMPLES

The present invention is further specifically described below by way of Examples, Test Examples, and Formulation Examples. However, the present invention is not limited thereto.

In the following Examples, the term "room temperature" refers to about 10° C. to about 35° C. The term "overnight" generally refers to 10 hours to 15 hours. In a reaction using a reagent or compound unstable against water or oxygen, a flask, syringe, cannula, and the like that had been dried by heating in advance were used, and the reaction was performed under a nitrogen atmosphere or under an argon atmosphere. Reduced-pressure concentration was performed using a diaphragm vacuum pump and a rotary evaporator. For high-performance liquid chromatography, there were used: JASCO PU-980 from JASCO Corporation as a pump; JASCO UV-4075 from JASCO Corporation as a UV detector; JASCO 807-IT from JASCO Corporation as an integrator; COSMOCIL 5C18-AR-II [Φ5 μm, 4.6 mm I.D.×150 mm] from Nacalai Tesque, Inc. as an analytical column; and COSMOCIL 5C18-AR-II Packed column [Φ5 μm, 20 mm I.D.×250 mm] from Nacalai Tesque, Inc. as a preparative column. A nuclear magnetic resonance spectrum was measured using JNM-ECA600 (600 MHz) manufactured by JEOL Ltd. For a $^1$H NMR spectrum, dimethyl sulfoxide (2.50 ppm) and methanol (3.30 ppm) were used as internal standards. Multiplicity was described with abbreviations: s (singlet), d (doublet), t (triplet), q (quartet), quin (quintet), and m (multiplet), and a broad signal was noted with brs. A coupling constant (J) was described in Hz. A proton peak of an alcohol, an amino group, a carboxylic acid, or the like, when too broad to be detected, is not described in some cases. For a high-resolution mass spectrum (HRMS), micro Tof focus (ESI-TOF) manufactured by Bruker was used. A protonated molecular ion is generally detected, but in the case of a salt, only a cation portion is detected.

In Examples below, the following abbreviations are used.
methanol-d4: deuterated methanol
DIPEA: N,N-diisopropylethylamine
Indole-FBnPYR: N-(3-{2-[2-(3-{4-[2-amino-9-(4-fluoro-benzyl)-6-oxo-6,9-dihydro-1H-purin-8-yl]-pyrazol-1-yl}-propoxy)-ethoxy]-ethoxy}-propyl)-2-oxo-2-(2-phenyl-1H-indol-3-yl)-acetamide
CCCP: carbonyl cyanide m-chlorophenyl hydrazone
DMF: N,N-dimethylformamide
DMSO-$d_6$: deuterated dimethyl sulfoxide
ESI: electrospray ionization
Et$_3$N: triethylamine
FBnNAC: (R)-2-amino-3-(2-amino-9-(4-fluorobenzyl)-6-oxo-6,9-dihydro-1H-purin-8-ylthio)propanoic acid
FBnNAC-linker: (R)-2-acetamido-3-(2-amino-9-(4-fluorobenzyl)-6-oxo-6,9-dihydro-1H-purin-8-ylthio)-N-(3-(2-(2-(3-aminopropoxy)ethoxy)ethoxy)propyl)propanamide
Indole-FBn: (R)-2-acetamido-3-[2-amino-9-(4-fluorobenzyl)-6-oxo-6,9-dihydro-1H-purin-8-ylsulfanyl]-N-{3-[2-(2-{3-[2-oxo-2-(2-phenyl-1H-indol-3-yl)-acetylamino]-propoxy}-ethoxy)-ethoxy]-propyl}propanamide
MS: mass spectrum
N.S.: not significant
HRMS: high-resolution mass spectrum
$^1$H NMR: proton nuclear magnetic resonance
PBS: phosphate buffered saline
PyBOP: (benzotriazol-1-yl-oxy)tripyrrolidinophosphonium hexafluorophosphate
TFA: trifluoroacetic acid Example 1

Synthesis of 4-(4-(3-(2-(2-(3-Aminopropoxy) ethoxy)ethoxy)propylcarbamoyl)phenyl)-1-methylpyridinium Trifluoroacetate 4-(4-Carboxy-phenyl)-1-methyl-pyridinium iodide (4.8 mg) was placed in a flask. Under an argon atmosphere at 40° C., DMF (95 μL), PyBOP (15.1 mg), TEA (4.1 μL), and diethylene glycol bis(3-aminopropyl) ether (6.4 μL) were added, and the mixture was stirred overnight. The reaction mixture was purified by HPLC (5C18-AR-II, mobile phase: water/acetonitrile (containing 0.1% TFA)) to afford the title compound (1.6 mg).

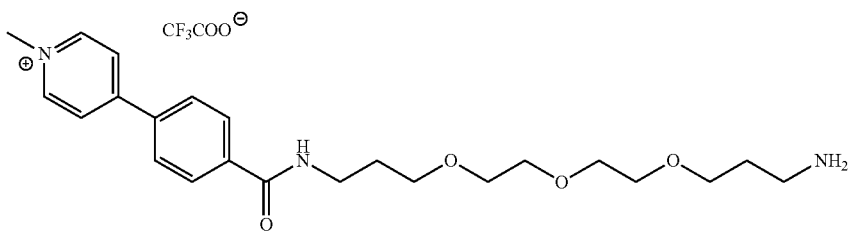 [SMILES: C[n+]1ccc(-c2ccc(C(=O)NCCCOCCOCCOCCCN)cc2)cc1 ; "CF3COO"]

HRMS:
Calcd for $C_{23}H_{34}N_3O_4$ [M]$^+$: 416.2544, found 416.2518
$^1$H NMR (600 MHz, DMSO-$d_6$) δ 1.16 (1H, t, J=7.3 Hz), 1.23-1.25 (1H, m), 1.73-1.79 (4H, m), 2.84 (2H, quin, J=5.5 Hz), 3.44-3.53 (12H, m), 4.33 (3H, s), 7.65 (2H, brs), 8.05 (2H, d, J=8.7 Hz), 8.16 (2H, d, J=8.7 Hz), 8.54 (2H, d, J=6.8 Hz), 8.70 (1H, t, 5.5 Hz), 9.04 (2H, d, J=6.8 Hz).

Example 2

Synthesis of (R)-4-[4-(3-{2-[2-(3-{2-Acetylamino-3-[2-amino-9-(4-fluoro-benzyl)-6-oxo-6,9-dihydro-1H-purin-8-ylsulfanyl]-propionylamino}-propoxy)-ethoxy]-ethoxy}-propylcarbamoyl)-phenyl]-1-methyl-pyridinium Trifluoroacetate 4-(4-(3-(2-(2-(3-Aminopropoxy)ethoxy)ethoxy)propylcarbamoyl)phenyl)-1-methylpyridinium trifluoroacetate (1.6 mg) was placed in a flask. Under an argon atmosphere, DMF (20 μL), PyBOP (3.1 mg), TEA (0.84 μL), and (R)-2-amino-3-(2-amino-9-(4-fluorobenzyl)-6-oxo-6,9-dihydro-1H-purin-8-ylthio)propanoic acid (FBnNAC) (2.6 mg) were added, and the mixture was stirred at room temperature for 7 hours. The reaction mixture was purified by HPLC (5C18-AR-II, mobile phase: water/acetonitrile (containing 0.1% TFA)) to afford the title compound (1.89 mg).

HRMS:
Calcd for $C_{43}H_{48}FN_9O_8S$ [M+H]$^+$: 870.3409, found 870.3396

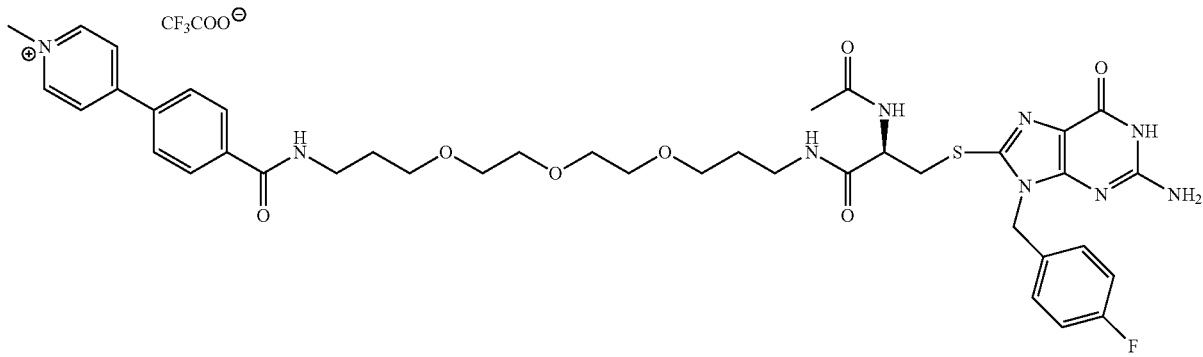 [SMILES: CC(=O)N[C@@H](CSc1nc2c(=O)[nH]c(N)nc2n1Cc1ccc(F)cc1)C(=O)NCCCOCCOCCOCCCNC(=O)c1ccc(-c2cc[n+](C)cc2)cc1 ; "CF3COO"]

HRMS:
Calcd for $C_{40}H_{49}FN_9O_7S$ [M]$^+$: 818.3454, found 818.3487

$^1$H NMR (600 MHz, DMSO-d$_6$) δ 1.83 (3H, s), 3.3-3.5 (12H, m), 1.58 (2H, quin, J=6.8 Hz), 1.74-1.77 (2H, m), 3.06-3.08 (6H, m), 4.32 (3H, s), 4.41-4.45 (1H, m), 5.06 (2H, s), 6.54 (2H, brs), 7.12-7.15 (4H, m), 8.02 (1H, t, J=5.5 Hz), 8.05 (2H, d, J=8.3 Hz), 8.15 (2H, d, J=8.3 Hz), 8.41 (1H, d, J=8.3 Hz), 8.53 (2H, d, J=6.4 Hz), 8.67 (1H, t, J=5.5 Hz), 9.03 (2H, d, J=6.4 Hz), 10.7 (1H, s).

Example 3

Synthesis of (R)-2-Acetylamino-3-[2-amino-9-(4-fluoro-benzyl)-6-oxo-6,9-dihydro-1H-purin-8-ylsulfanyl]-N-{3-[2-(2-{3-[2-oxo-2-(2-phenyl-1H-indol-3-yl)-acetylamino]-propoxy}-ethoxy)-ethoxy]-propyl}-propionamide (Indole-FBn)

Oxo-(2-phenyl-1H-indol-3-yl)-acetyl chloride (0.57 mg) was placed in a flask. Under an argon atmosphere at 0° C., DMF (6.8 µL), TEA (0.45 µL), and FBnNAC-linker (1.7 mg) were added, and the mixture was increased in temperature to room temperature and stirred for 7 hours. The reaction mixture was purified by HPLC (5C18-AR-II, mobile phase: water/acetonitrile (containing 0.1% TFA)) to afford the title compound (1.9 mg).

$^1$H NMR (600 MHz, DMSO-d$_6$) δ 1.42 (2H, quin, J=6.9 Hz), 1.59 (2H, quin, J=6.9 Hz), 1.83 (3H, s), 2.37-2.38 (2H, m), 2.52-2.60 (2H, m), 3.3-3.5 (16H, m), 4.42-4.44 (1H, m), 5.06 (2H, s), 7.13-7.16 (2H, m), 7.19 (2H, m), 7.21-7.27 (2H, m), 7.46-7.48 (4H, m), 7.54-7.55 (2H, m), 8.02 (1H, t, J=5.5 Hz), 8.06 (1H, d, J=7.8 Hz), 8.40 (1H, d, J=8.2 Hz), 8.43 (1H, t, J=5.5 Hz), 10.6 (1H, s), 12.4 (1H, s).

Example 4

Synthesis of (R)-N-(9-(4-(4-(((2-Amino-9-(4-fluorobenzyl)-6-oxo-6,9-dihydro-1H-purin-8-ylthio) methyl)-2,5-dioxo-10,13,16-trioxa-3,6-diazanonadecan-19-ylcarbamoyl)-2-carboxyphenyl)-6-(dimethylamino)-3H-xanthen-3-ylidene)-N-methylmethanaminium Trifluoroacetate 3-Carboxy-4-(6-(dimethylamino)-3-(dimethyliminio)-3H-xanthen-9-yl)benzoate (2.0 mg) was placed in a flask. Under an argon atmosphere, DMF (35.2 µL), PyBOP (1.9 mg), TEA (1.0 µL), and FBnNAC-linker (2.3 mg) were added, and the mixture was stirred at room temperature for 6 hours. Subsequently, the mixture was increased in temperature to 40° C. and further stirred for 4 hours. The reaction mixture was purified by HPLC (5C18-AR-II, mobile phase: water/acetonitrile (containing 0.1% TFA)) to afford the title compound (2.1 mg).

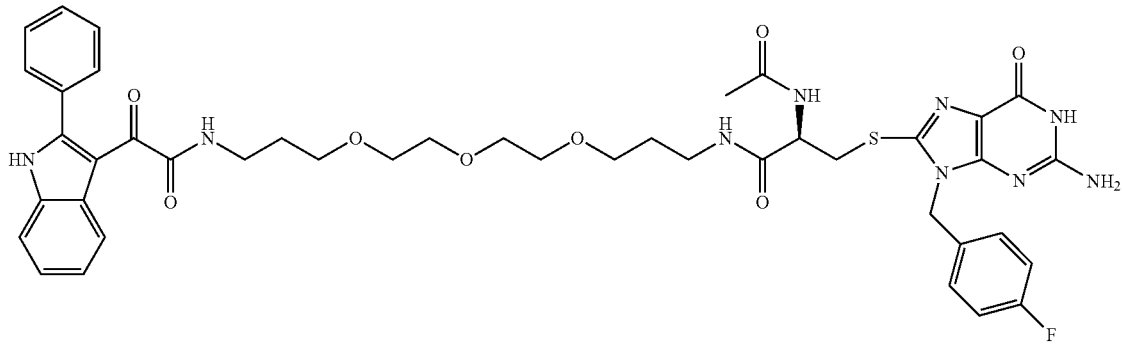 [SMILES: CC(=O)N[C@@H](CSc1nc2c(=O)[nH]c(N)nc2n1Cc1ccc(F)cc1)C(=O)NCCCOCCOCCOCCCNC(=O)C(=O)c1c(-c2ccccc2)[nH]c2ccccc12]

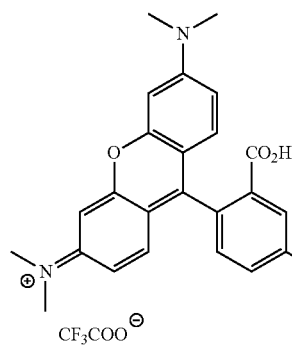

HRMS:
Calcd for $C_{52}H_{60}FN_{10}O_{10}S$ $[M]^+$: 1035.4193, found 1035.4186

$^1$H NMR (600 MHz, DMSO-$d_6$) δ 1.59 (2H, quin, J=7.1 Hz), 1.80-1.82 (5H, m), 2.89-2.90 (4H, m), 3.06-3.09 (14H, m), 3.27-3.50 (12H, m), 4.41-4.45 (1H, m), 5.06 (2H, s), 6.54 (2H, brs), 7.12-7.17 (4H, m), 7.58-7.60 (4H, m), 7.97-7.98 (1H, m), 8.02 (1H, t, J=5.5 Hz), 8.29 (1H, d, J=1.8 Hz) 8.35 (1H, dd, J=1.8, 8.2 Hz), 8.42 (1H, d, J=8.2 Hz), 8.71 (2H, s), 8.87 (1H, t, J=5.5 Hz), 10.66 (1H, s)

Example 5

Synthesis Method for Molecule (Following Illustration) Obtained by Bonding Protein Ligand Capable of Accumulating in Mitochondria and FBnNAC Mitochondrial Targeting Sequence

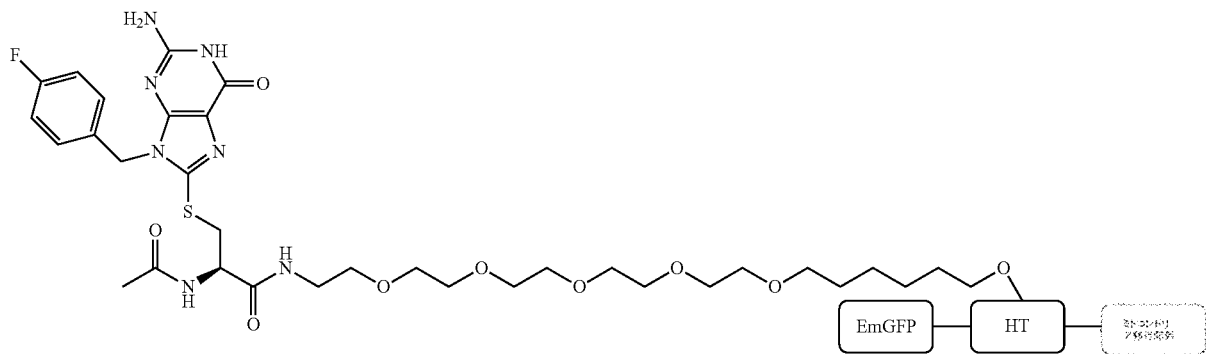

Figure 1:
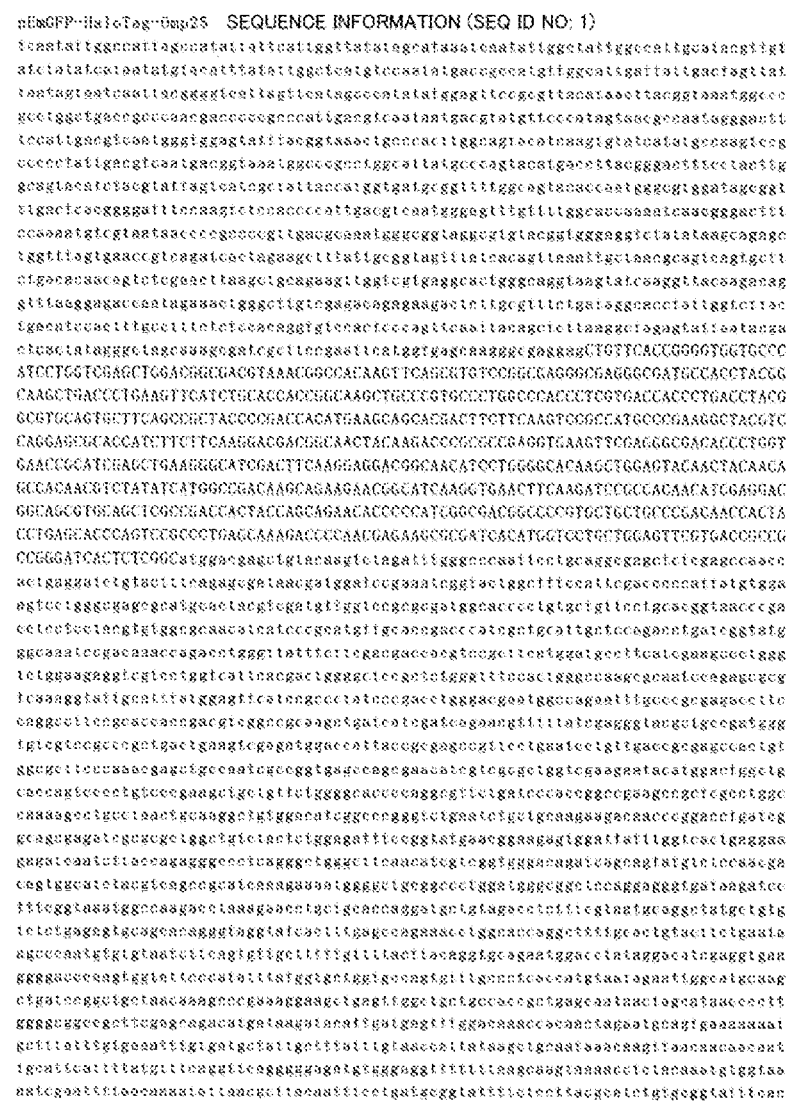

HeLa cells cultured in Dulbecco's Modified Eagle Medium (DMEM) were transfected with a plasmid pEmGFP-HaloTag-Omp25 encoding EmGFP-HaloTag-Omp25, and were allowed to stably express the protein. (R)-2-Acetamido-3-(2-amino-9-(4-fluorobenzyl)-6-oxo-6,9-dihydro-1H-purin-8-ylthio)-N-(21-chloro-3,6,9,12,15-pentaoxahenicosyl)propanamide was added thereto at a final concentration of 15 μM, and allowed to react with EmGFP-HaloTag-Omp25 under the conditions of 37° C./5% CO$_2$ for 4 hours to synthesize the title compound. - pEmGFP-HaloTag-Omp25 sequence information (SEQ ID NO: 1) is illustrated in FIG. 1 and FIG. 2.

Example 6

Assessment Method for Mitochondrial Degradation Effect (Mitophagy-Promoting Effect) of Compound Synthesized in Example 5

HeLa cells stably expressing EmGFP-HaloTag-Omp25 were seeded in Dulbecco's Modified Eagle Medium (DMEM) and cultured for 24 hours. The cells were divided into two groups. (R)-2-Acetamido-3-(2-amino-9-(4-fluorobenzyl)-6-oxo-6,9-dihydro-1H-purin-8-ylthio)-N-(21-chloro-3,6,9,12,15-pentaoxahenicosyl)propanamide was added to an experimental group at a final concentration of 15 μM, followed by incubation under the conditions of 37° C./5% CO$_2$ for 4 hours to synthesize the molecule of Example 5. In this case, a control group, to which no drug was added, was a group of cells free of the molecule of Example 5. Next, an uncoupler CCCP was added at a final concentration of 10 to both of the control group and the experimental group, followed by incubation for 4 hours to induce mitochondrial injury. The cells were washed with PBS and treated with a cell lysis solution containing a protease inhibitor to afford a cell extract. The cell extract was subjected to SDS-PAGE, and the level of a protein UQCRC1 present in the matrix of mitochondria was detected by western blotting. The relative value of the UQCRC1 level in the cells of the experimental group with respect to the control group was adopted as an activity value. The level of actin was used as an internal standard. The results are shown in FIG. 3. When the value is 1 or less, it is indicated that the degradation of the mitochondrial protein has been promoted. Data shown in the bar graph is mean±SEM in three independent experiments, and for P-values in Student's t-test, p<0.05 is represented by *, p<0.01 is represented by , and p<0.001 is represented by *.

Example 7

Figure 4:
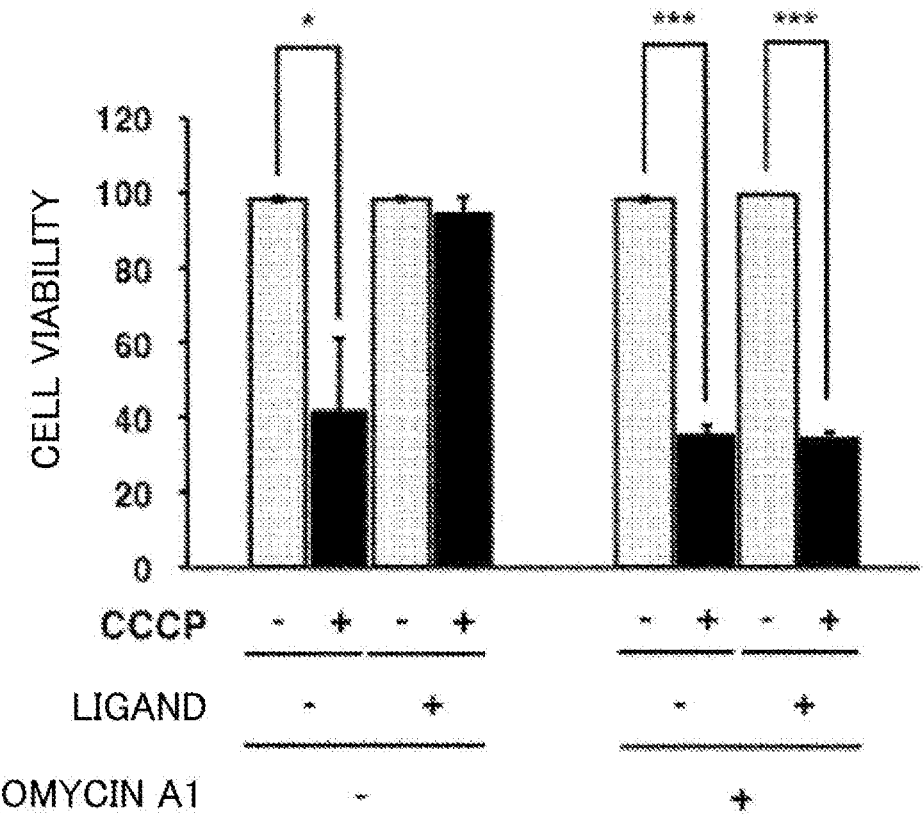
FIG. 4 shows test results of Example 7.

In order to cause mitochondrial injury, in this case, the uncoupler CCCP was used as a typical experimental condition. CCCP induces an abnormality in mitochondrial membrane potential.
Assessment Method for Cytoprotective Effect of Compound Synthesized in Example 5 Against Mitochondrial Injury
HeLa cells stably expressing EmGFP-HaloTag-Omp25 were seeded in Dulbecco's Modified Eagle Medium (DMEM) and cultured for 24 hours. The cells were divided into two groups. (R)-2-Acetamido-3-(2-amino-9-(4-fluorobenzyl)-6-oxo-6,9-dihydro-1H-purin-8-ylthio)-N-(21-chloro-3,6,9,12,15-pentaoxahenicosyl)propanamide was added to an experimental group at a final concentration of 15 µM, followed by incubation under the conditions of 37° C./5% $CO_2$ for 4 hours to synthesize the molecule of Example 5. In this case, a control group, to which no drug was added, was a group of cells free of the molecule of Example 5. Next, the uncoupler CCCP was added at a final concentration of 10 to both of the control group and the experimental group, followed by incubation for 4 hours to induce mitochondrial injury. The cells of each group were washed with PBS and subjected to fixing treatment with 4% paraformaldehyde, and then cell viability was calculated using a commercially available TUNEL apoptosis analysis kit (AAT Bioquest, Inc.). Viability (%) under each condition when the cell viability of the control group is defined as 100(%) is shown in FIG. 4 as a bar graph. In the legend of the graph, the molecule of Example 5 is referred to as "ligand" for simplicity.

Example 8

Assessment Method for Cytoprotective Effect of Compound of Example 3, (R)-2-Acetylamino-3-[2-amino-9-(4-fluoro-benzyl)-6-oxo-6,9-dihydro-1H-purin-8-ylsulfanyl]-N-{3-[2-(2-{3-[2-oxo-2-(2-phenyl-1H-indol-3-yl)-acetylamino]-propoxy}-ethoxy)-ethoxy]-propyl}-propionamide (Indole-FBn), Against Mitochondrial Injury, and Confirmation of Inhibition of Cytoprotective Effect with Autophagy Inhibitor (Bafilomycin A1: Baf A1)

Cell Viability under Condition of Treating Cells with Indole-FBn and CCCP (Test Group):
HeLa cells seeded in Dulbecco's Modified Eagle Medium (DMEM) in a 96-well plate at 30,000 cells/well were incubated under the conditions of 37° C./5% $CO_2$ overnight. Indole-FBn was added to the medium at a final concentration of 1 µM, followed by further incubation for 10 hours. At this time, nuclear staining by Hoechst33342 staining was performed for 30 minutes from 9 hours and 30 minutes to 10 hours after the addition of Indole-FBn.

Subsequently, the uncoupler CCCP was added at a final concentration of 10 µM, followed by further incubation for 2 hours to induce mitochondrial injury. Cells in each of which DNA fragmentation was found in the nucleus were judged to be dead cells, and cell viability was calculated by the following equation.

Cell viability (%)=100×(number of cells in which DNA fragmentation is observed)/(total number of cells)

The cell viability immediately before the CCCP treatment and the cell viability after 2 hours of the CCCP treatment are shown as a bar graph to enable comparison.

Figure 5:
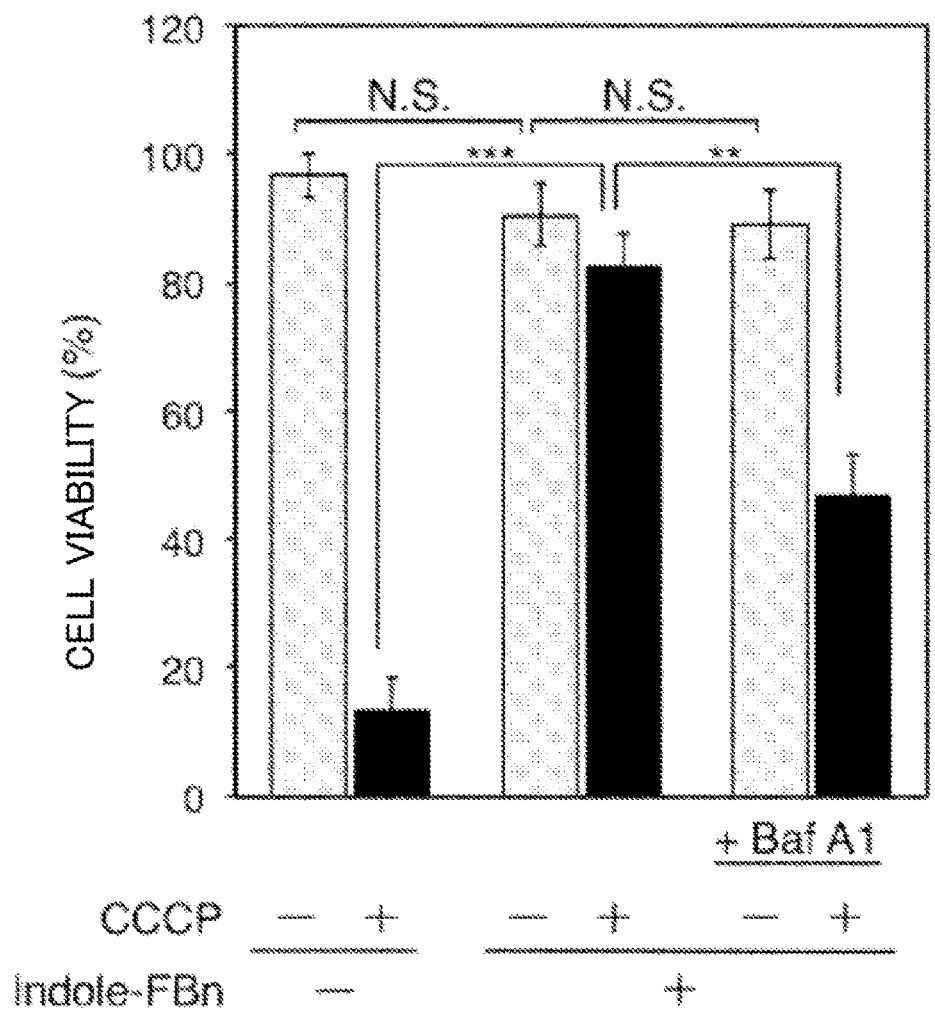
FIG. 5 shows test results of Example 8.

Cell Viability Under Condition of Not Treating Cells with Indole-FBn (Control Group):
HeLa cells seeded in Dulbecco's Modified Eagle Medium (DMEM) in a 96-well plate at 30,000 cells/well were incubated under the conditions of 37° C./5% $CO_2$ for 1 day, and then subjected to nuclear staining by Hoechst33342 staining. Subsequently, the uncoupler CCCP was added to half the wells at a final concentration of 10 µM, followed by further incubation for 2 hours to induce mitochondrial injury (non-Indole-FBn-treated and CCCP-treated condition). Cells in each of which DNA fragmentation was found in the nucleus were judged to be dead cells, and cell viability was calculated. In addition, cell viability was also calculated for the non-CCCP-treated wells (non-treated condition for both Indole-FBn and CCCP). The results are shown in FIG. 5.

The results of the above-mentioned experiment revealed that the addition of Indole-FBn significantly suppressed cell death due to mitochondrial injury.

Bafilomycin A1 (Baf A1) is known to inhibit autophagy via lysosome function inhibition. In view of this, in the above-mentioned experimental operations, Baf A1 was allowed to coexist, and the involvement of the autophagy mechanism was confirmed as described below. To HeLa cells incubated in DMEM medium overnight, Baf A1 was added in advance, 2 hours before Indole-FBn treatment, so as to have a final concentration of 200 nM. Without the removal of Baf A1 by washing, Indole-FBn was added to the medium, and the rest of the experiment was performed in conformity with the above-mentioned operations (treated condition with all of Indole-FBn, CCCP, and Baf A1). As a result, it was revealed that the cytoprotective effect exhibited by Indole-FBn under the CCCP-treated condition was significantly inhibited by the autophagy inhibitor Baf A1.

Data in the bar graph is mean±SEM obtained from three independent trials, and for P-values in Student's t-test, p<0.01 is represented by  and p<0.001 is represented by *.

Example 9

Synthesis of 4-[4-(3-{2-[2-(3-{4-[2-Amino-9-(4-fluoro-benzyl)-6-oxo-6,9-dihydro-1H-purin-8-yl]-pyrazol-1-yl1}-propoxy)-ethoxy]-ethoxy}-propylcarbamoyl)-phenyl]-1-methyl-pyridinium Trifluoroactate

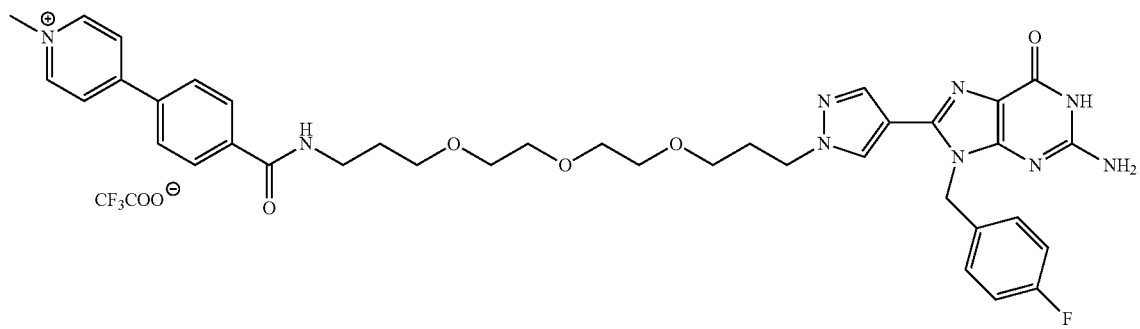

4-(1-Methylpyridinium-4-yl)benzoate (2.00 mg) was placed in a flask. Under an argon atmosphere, DMF (0.95 mL), PyBOP (9.84 mg), DIPEA (4.90 µL), and 2-amino-8-[1-(3-{2-[2-(3-amino-propoxy)-ethoxy]-ethoxy}-propyl)-1H-pyrazol-4-yl]-9-(4-fluoro-benzyl)-1,9-dihydro-purin-6-one (4.95 mg) were added, and the mixture was stirred at room temperature for 8 hours. The reaction mixture was purified by HPLC (5C18-AR-II, mobile phase: water/acetonitrile (containing 0.1% TFA)) to afford the title compound (1.75 mg).

HRMS:

Calcd for $C_{38}H_{43}FN_9O_5$ [M−$CF_3COO^-$]$^+$: 724.3366, found 724.3366

1H NMR (600 MHz, methanol-d4) δ 1.89-1.85 (2H, quin, J=6.42 Hz), 2.07-2.03 (2H, quin, J=6.42 Hz), 3.35-3.33 (2H, t, J=5.52 Hz), 3.50-3.47 (4H, m), 3.64-3.57 (8H, m), 4.29-4.26 (2H, t, J=6.9 Hz), 4.42 (3H, s), 5.50 (2H, s), 7.09-7.04 (2H, t, J=8.7 Hz), 7.18-7.16 (2H, d, J=5.52 Hz), 7.84 (1H, s), 8.01-8.00 (2H, d, J=6.9 Hz), 8.05-8.03 (2H, d, J=6.9 Hz), 8.08 (1H, s), 8.40 (2H, d, J=6.72 Hz), 8.90 (2H, d, J=6.9 Hz).

Example 10

Synthesis of N-(3-{2-[2-(3-{4-[2-Amino-9-(4-fluoro-benzyl)-6-oxo-6,9-dihydro-1H-purin-8-yl]-pyrazol-1-yl}-propoxy)-ethoxy]-ethoxy}-propyl)-2-oxo-2-(2-phenyl-1H-indol-3-yl)-acetamide

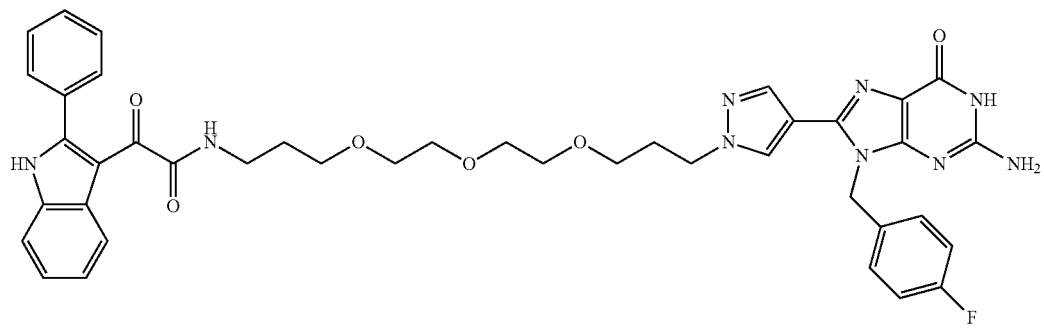 [SMILES: Nc1nc2c(nc(-c3cnn(CCCOCCOCCOCCCNC(=O)C(=O)c4c(-c5ccccc5)[nH]c5ccccc45)c3)n2Cc2ccc(F)cc2)c(=O)[nH]1]

HRMS:

Oxo-(2-phenyl-1H-indol-3-yl)-acetic acid (7.5 mg) and 2-amino-8-[1-(3-{2-[2-(3-amino-propoxy)-ethoxy]-ethoxy}-propyl)-1H-pyrazol-4-yl]-9-(4-fluoro-benzyl)-1,9-dihydro-purin-6-one (15 mg) were placed in a flask. Under an argon atmosphere, DMF (2.8 mL), PyBOP (22 mg), and DIPEA (15 µL) were added, and the mixture was stirred at room temperature for 13 hours. The reaction mixture was concentrated under reduced pressure, and the resultant residue was purified by HPLC (5C18-AR-II, mobile phase: water/acetonitrile (containing 0.1% TFA)) to afford the title compound (9.5 mg).

Calcd for $C_{41}H_{42}FN_9O_6$ [M+H]$^+$: 776.3315, found 776.3315

1H NMR (600 MHz, methanol-d4) δ 1.51 (2H, quin, J=6.4 Hz), 2.05 (2H, quin, J=6.4 Hz), 2.92 (2H, t, J=6.8 Hz), 3.32 (2H, t, J=5.9 Hz), 3.41 (2H, t, J=5.9 Hz), 3.44-3.46 (2H, m), 3.52-3.54 (4H, m), 3.55-3.57 (2H, m), 4.27 (2H, t, J=6.8 Hz), 5.47 (2H, s), 7.02-7.07 (2H, m), 7.17-7.21 (3H, m), 7.23-7.25 (1H, m), 7.42-7.49 (4H, m), 7.54-7.56 (2H, m), 7.88 (1H, s), 8.08-8.10 (1H, m), 8.19 (1H, s).

Example 11

Synthesis of {9-[4-(3-{2-[2-(3-{4-[2-Amino-9-(4-fluoro-benzyl)-6-oxo-6,9-dihydro-1H-purin-8-yl]-pyrazol-1-yl}-propoxy)-ethoxy]-ethoxy}-propylcarbamoyl)-2-carboxy-phenyl]-6-dimethylamino-xanthen-3-ylidene}-dimethyl-ammonium Trifluoroacetate

[9-(2,4-Dicarboxy-phenyl)-6-dimethylamino-xanthen-3-ylidene]-dimethyl-ammonium trifluoroacetate (4.4 mg) and 2-amino-8-[1-(3-{2-[2-(3-amino-propoxy)-ethoxy]-ethoxy}-propyl)-1H-pyrazol-4-yl]-9-(4-fluoro-benzyl)-1,9-dihydro-purin-6-one (4.2 mg) were placed in a flask. Under an argon atmosphere, DMF (0.8 mL), PyBOP (9.4 mg), and DIPEA (6.3 µL) were added, and the mixture was stirred at room temperature for 5 hours. The reaction mixture was concentrated under reduced pressure, and the resultant residue was purified by HPLC (5C18-AR-II, mobile phase: water/acetonitrile (containing 0.1% TFA)) to afford the title compound (1.6 mg).

HRMS:

Calcd for $C_{50}H_{54}FN_{10}O_8$ [M−CF$_3$COO$^-$]$^+$: 941.4105, found 941.4105

1H NMR (600 MHz, methanol-d4) δ 1.92 (2H, quin, J=6.4 Hz), 2.06 (2H, quin, J=6.4 Hz), 3.30-3.32 (12H, m), 3.34-3.36 (2H, m), 3.50-3.55 (4H, m), 3.60-3.66 (8H, m), 4.30 (2H, t, J=6.4 Hz), 5.52 (2H, s), 6.97 (2H, d, J=2.3 Hz), 7.02-7.12 (6H, m), 7.19-7.22 (2H, m), 7.52 (1H, d, J=8.3 Hz), 7.88 (1H, s), 8.18 (1H, s), 8.23 (1H, dd, J=1.8, 5.9 Hz), 8.73 (1H, d, J=1.8 Hz).

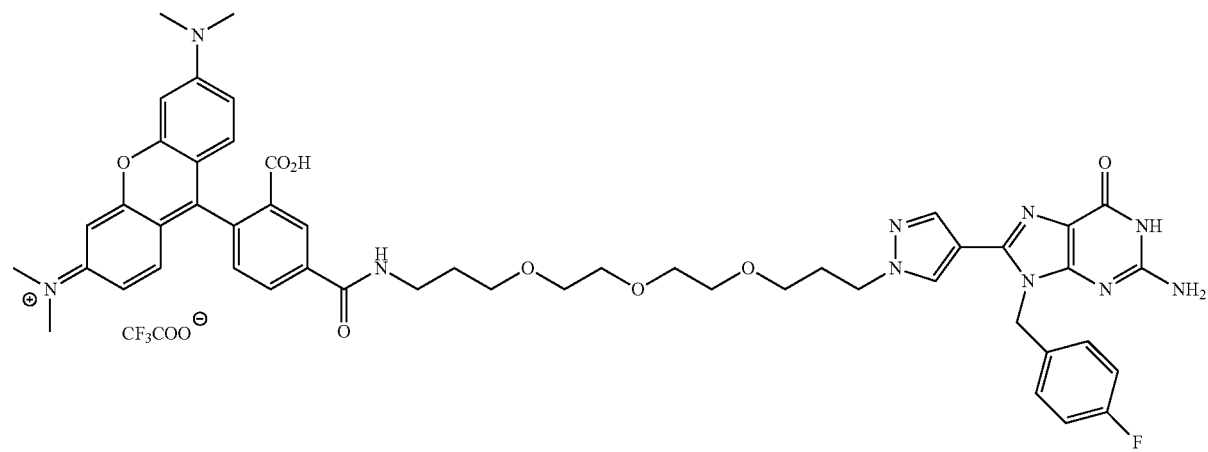

Example 12

Synthesis of (R) -N¹-(4-(3-Amino-6-(thiophen-2-yl)-4-(trifluoromethyl)thieno[2,3-b]pyridine-2-carbonyl)phenyl)-N²-(4-(((2-amino-9-(4-fluorobenzyl)-6-oxo-6,9-dihydro-1H-purin-8-yl)thio)methyl)-2,5-dioxo-10,13,16-trioxa-3,6-diazanonadecan-19-yl) oxalamide

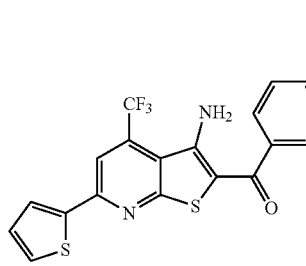 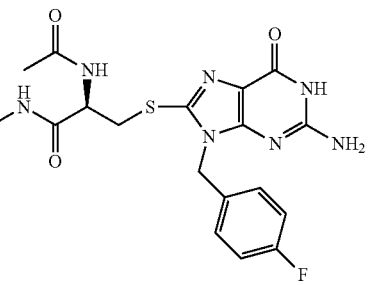

3-(3-{2-[2-(3-Amino-propoxy)-ethoxy]-ethoxy}-propylamino)-N-[4-(3-amino-6-thiophen-2-yl-4-trifluoromethyl-thieno[2,3-b]pyridine-2-carbonyl)-phenyl]-2-oxo-propionamide (1.6 mg) was placed in a flask, and under an argon atmosphere, DMF (45 μL), TEA (0.7 μL), and FBnNAC (1.0 mg) were added. The mixture was stirred at room temperature for 5 hours, and then PyBOP (2.9 mg) and TEA (0.7 μL) were added. The mixture was stirred overnight. The reaction mixture was purified by HPLC (5C18-AR-II, mobile phase: water/acetonitrile (containing 0.1% TFA)) to afford the title compound (1.1 mg).

HRMS:
Calcd for $C_{48}H_{49}FN_{11}O_9S_3$ [M+H]⁺: 1096.2891, found 1096.2892

1H NMR (600 MHz, DMSO-d₆) δ 1.57-1.62 (2H, quin, J=6.9 Hz), 1.72-1.76 (2H, quin, J=7.2 Hz), 1.82 (3H, s), 3.26-3.45 (18H, m), 4.42-4.46 (1H, m), 5.06 (2H, s), 6.52 (2H, brs), 7.12-7.15 (2H, m), 7.18-7.20 (2H, m), 7.26-7.27 (1H, dd, J=3.67, 5.04 Hz), 7.73 (2H, brs), 7.86-7.87 (1H, dd, 0.92, 5.04 Hz), 7.82-7.84 (2H, d, J=8.71 Hz), 8.00-8.01 (2H, d, J=8.71 Hz), 8.03 (1H, t, J=5.61 Hz), 8.26-8.27 (1H, dd, J=0.91, 3.66 Hz), 8.33 (1H, s), 8.40-8.41 (1H, d, J=8.25 Hz), 9.03 (1H, t, J=6.00 Hz), 10.64 (1H, s), 10.94 (1H, s).

Example 13

Indole-FBn Promotes Degradation of Injured Mitochondria (Living Cell Imaging Method)

HeLa cells cultured in Dulbecco's Modified Eagle Medium (DMEM) were transfected with the plasmid pEmGFP-HaloTag-Omp25 containing a gene sequence encoding the EmGFP-HaloTag-Omp25 fusion protein localized on the mitochondrial outer membrane, and were allowed to stably express the protein. As a result, mitochondria in the cells were able to be observed using green fluorescence as an indicator.

A red fluorescent dye MitoTracker Red CMXRos (Thermo Fisher Scientific, M7513) was added thereto, followed by incubation for 30 minutes to stain mitochondria. At this stage, the mitochondria in the cells had been stained in two colors by EmGFP-HaloTag-Omp25 and MitoTracker Red CMXRos. Subsequently, MitoTracker Red CMXRos in the medium was removed by medium exchange. Mitochondria to be biosynthesized after this operation can only be detected with green fluorescence, and are not to be detected with red fluorescence. This difference was utilized to observe the degradation process of mitochondria by living cell imaging.

The cells were divided into two groups. Indole-FBn was added to an experimental group at a final concentration of 10 Indole-FBn was not added to a control group. In order to observe living cells at a fixed point for a long period of time, a culture vessel was fixed to a stage-top incubator (37° C., 5% $CO_2$) mounted on a fluorescence microscope (KEYENCE, BX9000), and all the subsequent operations were performed on the microscope. After 10 hours from the addition of Indole-FBn, 10 CCCP was simultaneously added to the experimental group and the control group, and incubation was continued.

Figure 6:
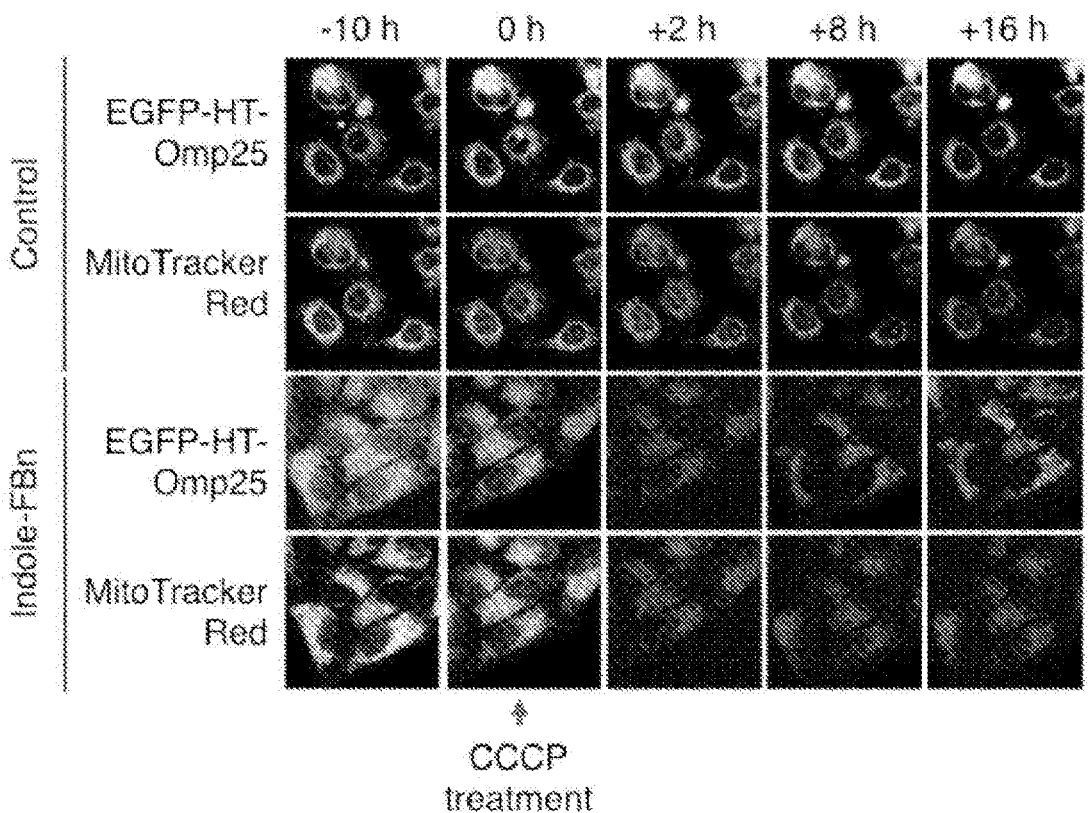
FIG. 6 shows test results of Example 13.
Figure 7:
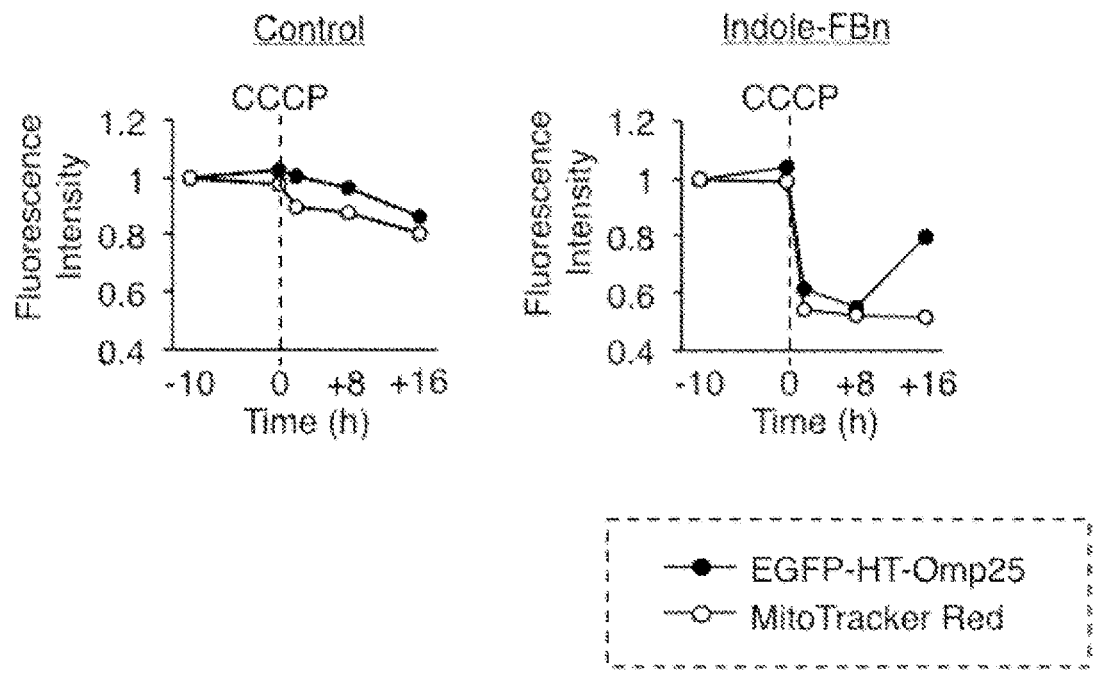
FIG. 7 shows test results of Example 13.

The signals of EmGFP-HaloTag-Omp25 and MitoTracker Red CMXRos at the time of the addition of Indole-FBn (−10 h), the time of the addition of CCCP (0 h), 2 hours after the addition of CCCP (+2 h), 4 hours after the addition of CCCP (+8 h), and 16 hours after the addition of CCCP (+16 h) are shown in FIG. 6 and FIG. 7. In the graphs, the intensities of the signals of EmGFP-HaloTag-Omp25 (green fluorescence) and MitoTracker Red CMXRos (red fluorescence) in the photographs shown in FIG. 6 are shown as relative values with the respective intensities at −10 h being defined as 1. Image analysis was performed with ImageJ (National Institutes of Health). The results are shown in FIG. 6 and FIG. 7.

As apparent from the graphs, in the cells of the Indole-FBn-treated group, green and red signal intensities were reduced after the addition of CCCP (2 h, 8 h). This indicates that injured mitochondria were degraded when CCCP was added. In addition, a comparison of the graphs for 8 hours and 16 hours after the addition of CCCP showed that, only in the Indole-FBn-treated group, the green fluorescence intensity was increased, indicating the production of new mitochondria.

The living cell imaging experiment described above showed that Indole-FBn promoted both the removal of injured mitochondria and the production of new mitochondria.

Example 14

JC-1 Staining

Detroit532 cells, which were Down syndrome patient foreskin-derived fibroblasts, were cultured in Eagle's Minimum Essential Medium. The cells were divided into two groups. A compound (Indole-FBn) was added to an experimental group at a final concentration of 10 µM, and was not added to a control group, followed by incubation for 3 days (37° C., 5% CO₂). The cells of each group were each stained with JC-1 (abcam, 113850).

Figure 8:
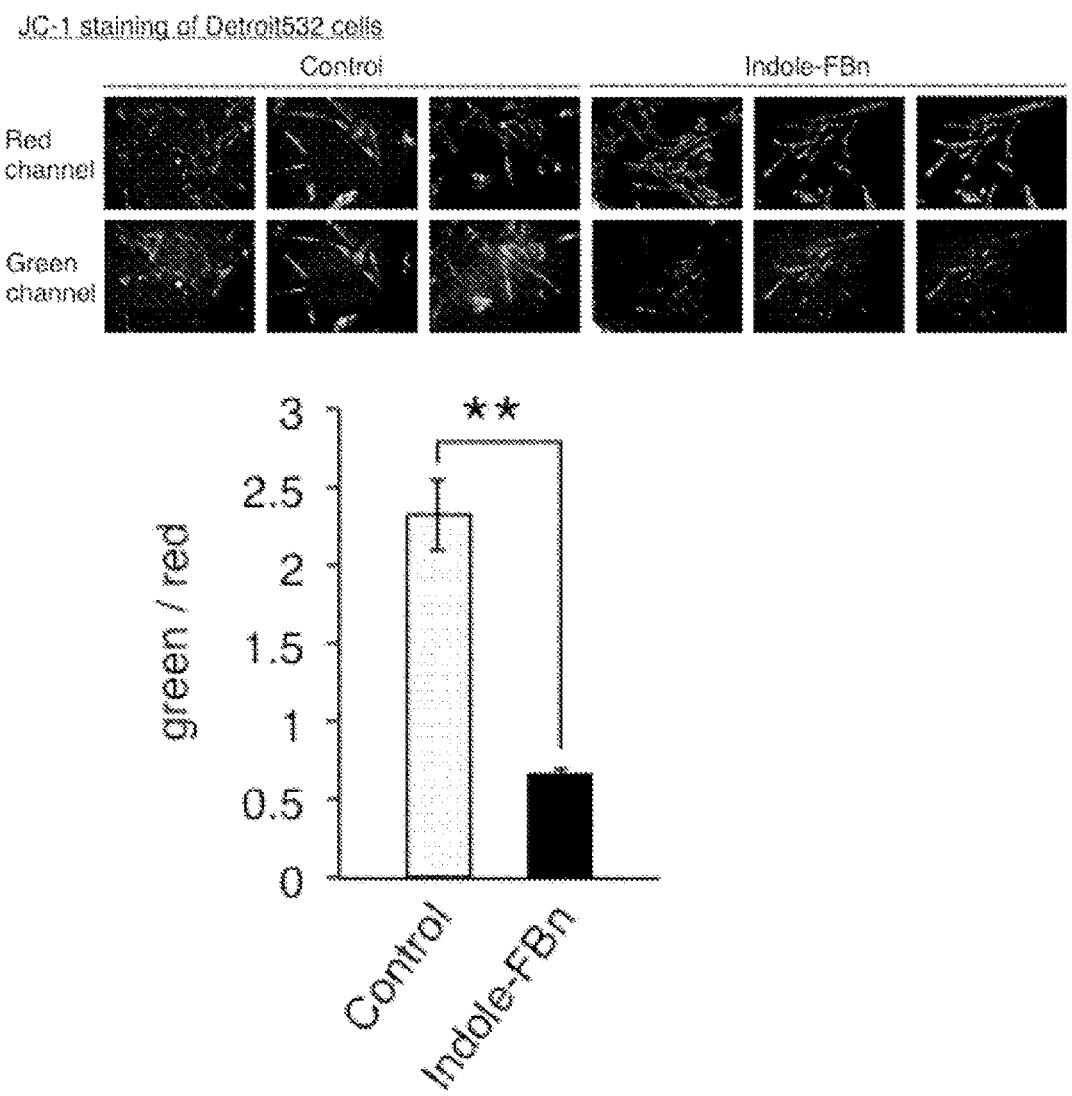
FIG. 8 shows test results of Example 14.

The JC-1 dye accumulates in mitochondria having a normal membrane potential to emit red fluorescence. Meanwhile, its localization is lost from mitochondria having an abnormal membrane potential and green fluorescence is emitted. That is, in a JC-1 staining image, a lower "green/red fluorescence intensity ratio" means that the membrane potential of mitochondria is kept more normal. Staining images were analyzed with ImageJ (National Institute of Health), and the "green/red fluorescence intensity ratio" is shown as a graph. The results are shown in FIG. 8. Error bars represent standard deviations obtained from data from three independent experiments.

The results show that the quality of mitochondria reduced by a disease as in, for example, Down syndrome-derived cells is significantly improved by adding the compound.

Example 15

Assessment of Mitophagy Induction with Indole-FBn in Down Syndrome Patient-Derived Detroit532 Cells In order to confirm that the Indole-FBn compound treatment in Example 14 induces the degradation (mitophagy) of mitochondria, analysis was performed using Mtphagy dye (Dojindo, MD01) as a mitophagy detection kit. The use of this reagent allows mitochondria under mitophagy degradation to be selectively detected as bright spots under a fluorescence microscope. A larger number of bright spots per cell indicates the occurrence of more active mitophagy.

Figure 9:
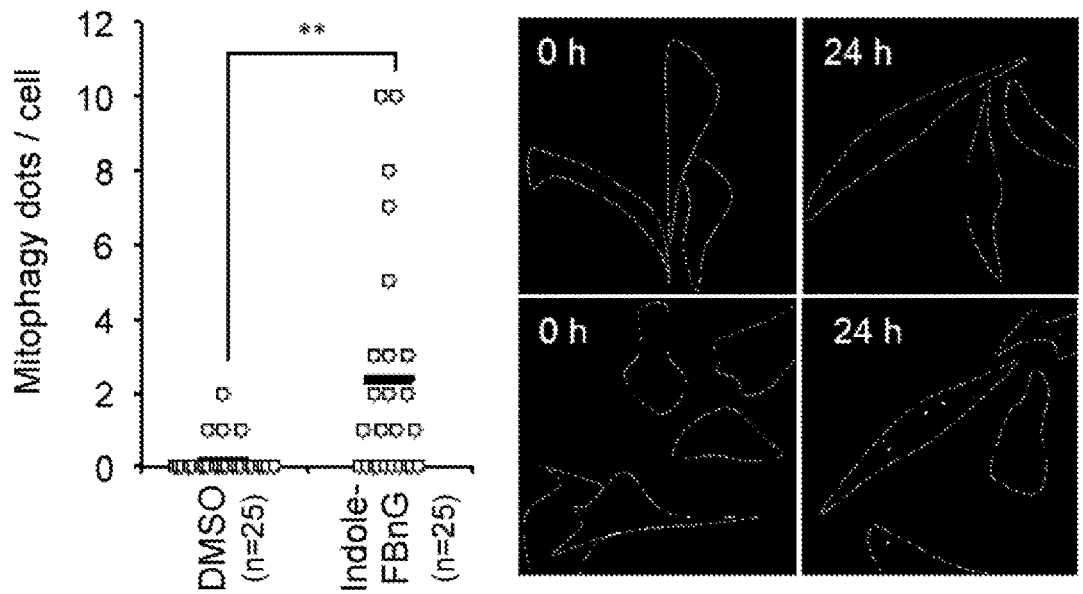
FIG. 9 shows test results of Example 15.

Mtphagy dye was added to Detroit532 cells. After 30 minutes from the addition, Mtphagy dye was removed by washing, the medium was changed to a fresh one, and Indole-FBnG was added at a final concentration of 10 µM. Meanwhile, a group of cells treated with DMSO was used as a control group. After 24 hours from the addition of Indole-FBn, bright spots of Mtphagy Dye were observed with a fluorescence microscope (FIG. 9). The photographs were taken of the cells of the control group and the drug-administered group immediately after the Indole-FBn treatment (0 hours) and after 24 hours. 25 cells of both groups were each observed, and the number of Mtphagy Dye bright spots (Mitophagy dots) per cell was plotted as white circles on the vertical axis. The Wilcoxon test was performed for the control group and the drug-administered group, and p<0.01 was represented by **.

Example 16

Figure 10:
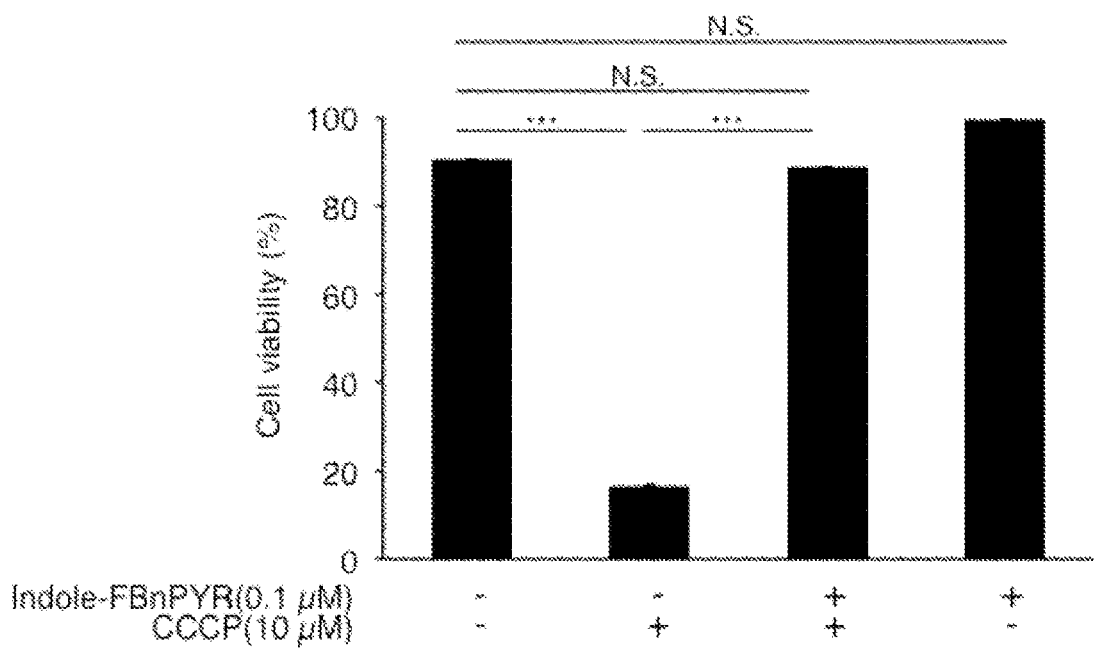
FIG. 10 shows test results of Example 16.

Assessment of Cytoprotective Effect of Indole-FBnPYR (Example 10) Against Mitochondrial Injury HeLa cells were seeded in Dulbecco's Modified Eagle Medium (DMEM) and cultured for 24 hours. The cells were divided into two groups. Indole-FBnPYR was added to an experimental group at a final concentration of 0.1 µM, followed by incubation under the conditions of 37° C./5% CO₂ for 4 hours. In this case, a control group, to which Indole-FBnPYR was not added, was a group of cells free of any drug. Next, the uncoupler CCCP was added at a final concentration of 10 to both of the control group and the experimental group, followed by incubation for 10 hours to induce mitochondrial injury. The cells of each group were washed with PBS and subjected to fixing treatment with 4% paraformaldehyde, and then cell viability was calculated using a TUNEL apoptosis analysis kit (Promega, DeadEnd Fluorometric TUNEL System). The results are shown in FIG. 10.

Error bars represent standard errors (n=3).

The invention claimed is:

1. A pharmaceutical comprising:
a compound or a salt thereof, the compound containing
a ligand which binds to or accumulates in mitochondria,
a substituent represented by the following general formula (1):

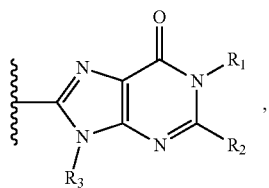
(1)

and
a linker, a first end of the linker being bound to the ligand and a second end of the linker being bound to the substitutent;
where $R^1$, $R^2$, and $R^3$ are identical to or different from each other,
wherein $R^1$ represents a hydrogen atom or a hydrocarbon group,
wherein $R^2$ represents a hydrogen atom, a hydrocarbon group that may be substituted, an amino group that may be substituted, or a carbamoyl group that may be substituted,
wherein $R^3$ represents a hydrogen atom or a hydrocarbon group that may be substituted,
wherein the pharmaceutical is effective to treat a disease that is treatable by degradation of injured mitochondria based on an autophagy mechanism, and
wherein the ligand is a monovalent substituent obtained by removing one hydrogen atom from any one of following compounds, wherein at least one hydrogen atom bonded to the unsaturated ring structure of the compounds may be substituted:

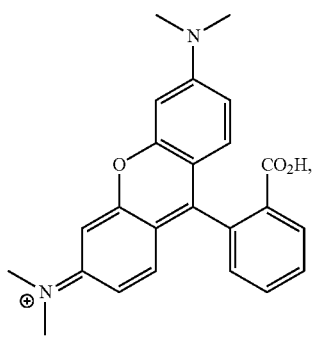

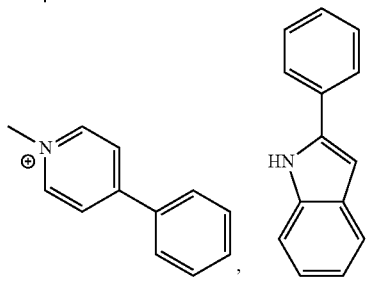

-continued

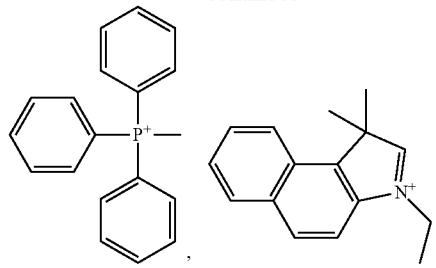

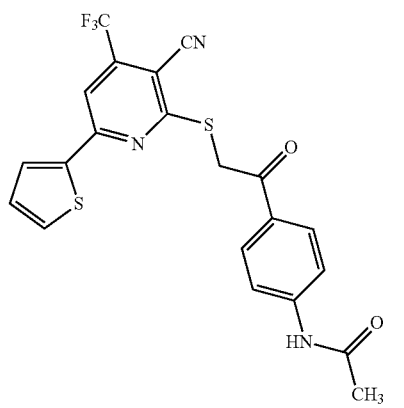

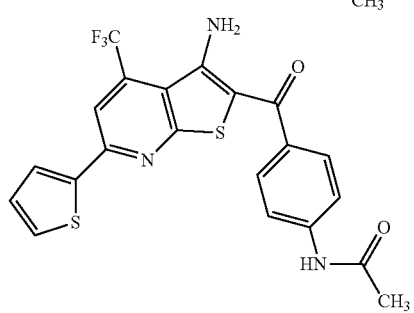

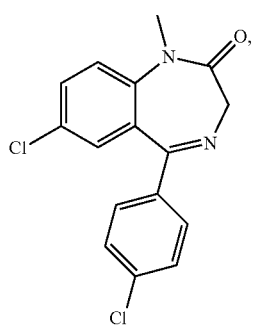

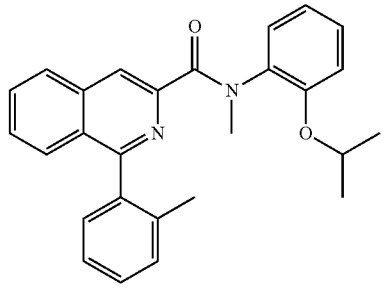

-continued

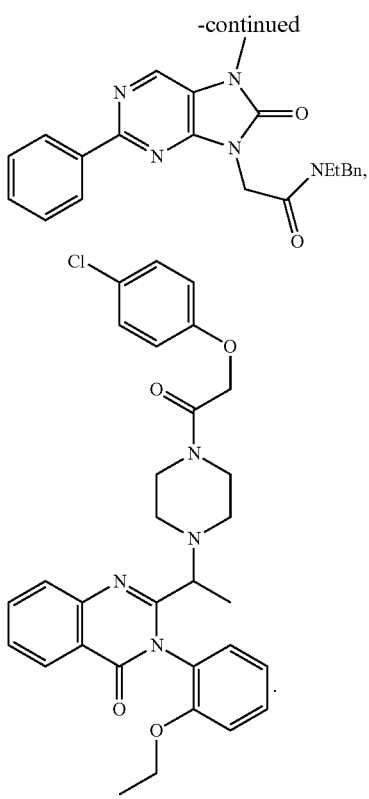

2. The pharmaceutical according to claim 1, wherein the disease that is treatable by degradation of injured mitochondria based on an autophagy mechanism is a neurodegenerative disease, cancer, an inflammatory disease, an age-related disease, a metabolic disease, a mitochondrial disease, or Down syndrome.

3. A compound or a salt thereof, the compound comprising:
   a ligand which binds to or accumulates on a mitochondrial surface,
   a substituent represented by the following general formula (1):

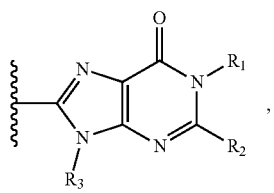

(1)

and
   a linker, a first end of the linker being bound to the ligand and a second end of the linker being bound to the substitutent;
   where $R^1$, $R^2$, and $R^3$ are identical to or different from each other,
   wherein $R^1$ represents a hydrogen atom or a hydrocarbon group,
   wherein $R^2$ represents a hydrogen atom, a hydrocarbon group that may be substituted, an amino group that may be substituted, or a carbamoyl group that may be substituted,
   wherein $R^3$ represents a hydrogen atom or a hydrocarbon group that may be substituted,
   wherein the compound or the salt thereof inducing degradation of injured mitochondria based on an autophagy mechanism, and
   wherein the ligand is a monovalent substituent obtained by removing one hydrogen atom from any one of following compounds, wherein at least one hydrogen atom bonded to the unsaturated ring structure of the compounds may be substituted:

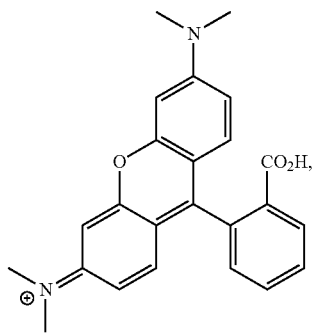

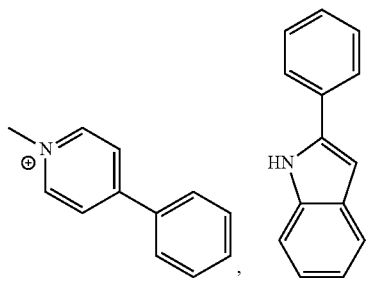

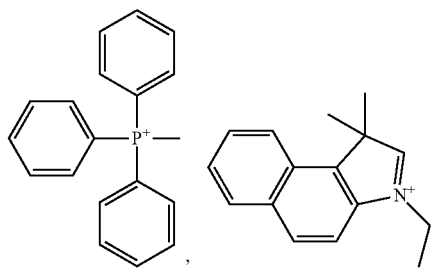

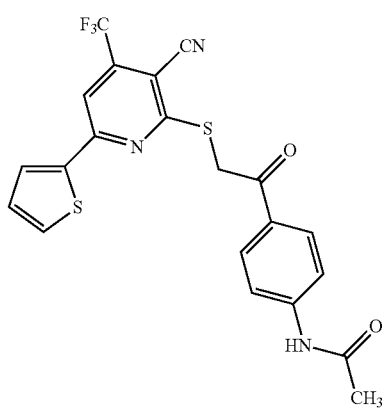

-continued

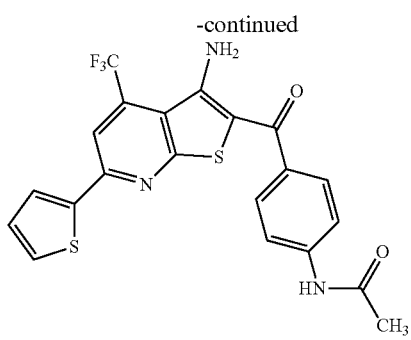

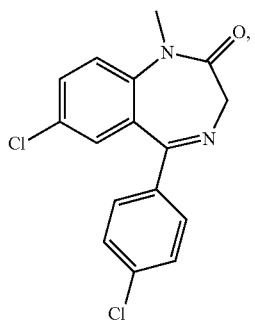

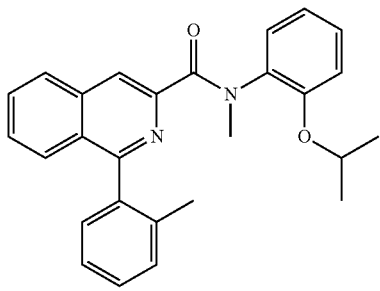

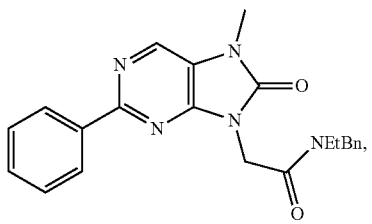

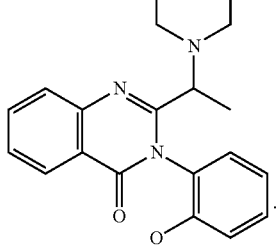

4. The compound or the salt thereof according to claim 3, wherein the compound or the salt thereof is effective to treat a disease that is treatable by degradation of injured mitochondria based on an autophagy mechanism.

5. The pharmaceutical according to claim 1, wherein the ligand is a monovalent substituent obtained by removing one hydrogen atom from any one of the following compounds:

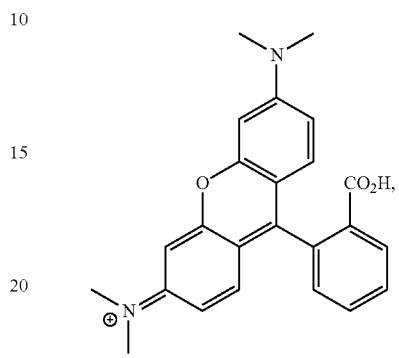

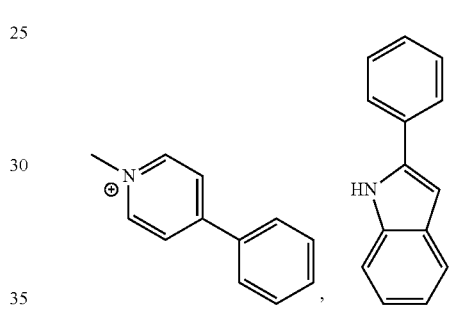

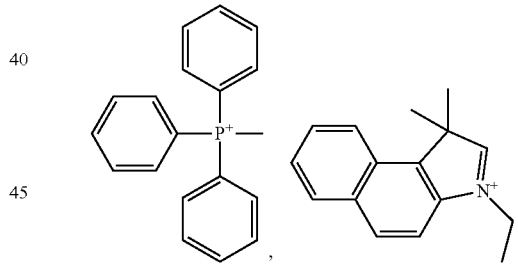

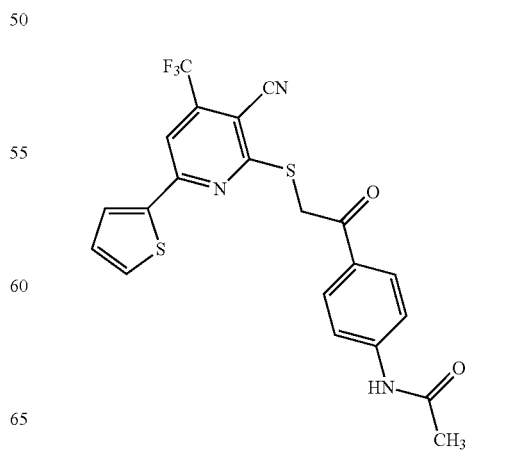

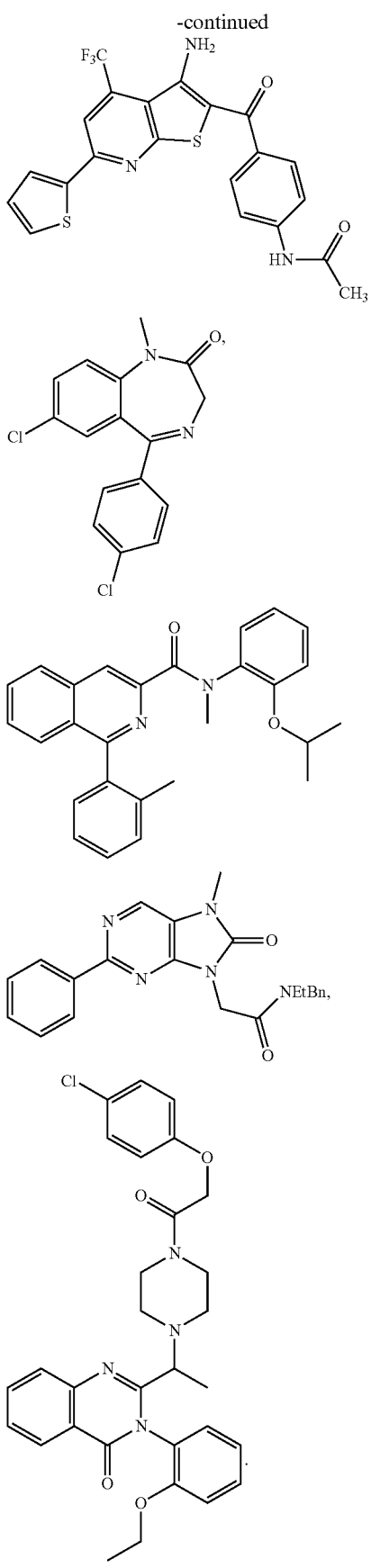
6. The compound or the salt thereof according to claim 3, wherein the ligand is a monovalent substituent obtained by removing one hydrogen atom from any one of the following compounds:
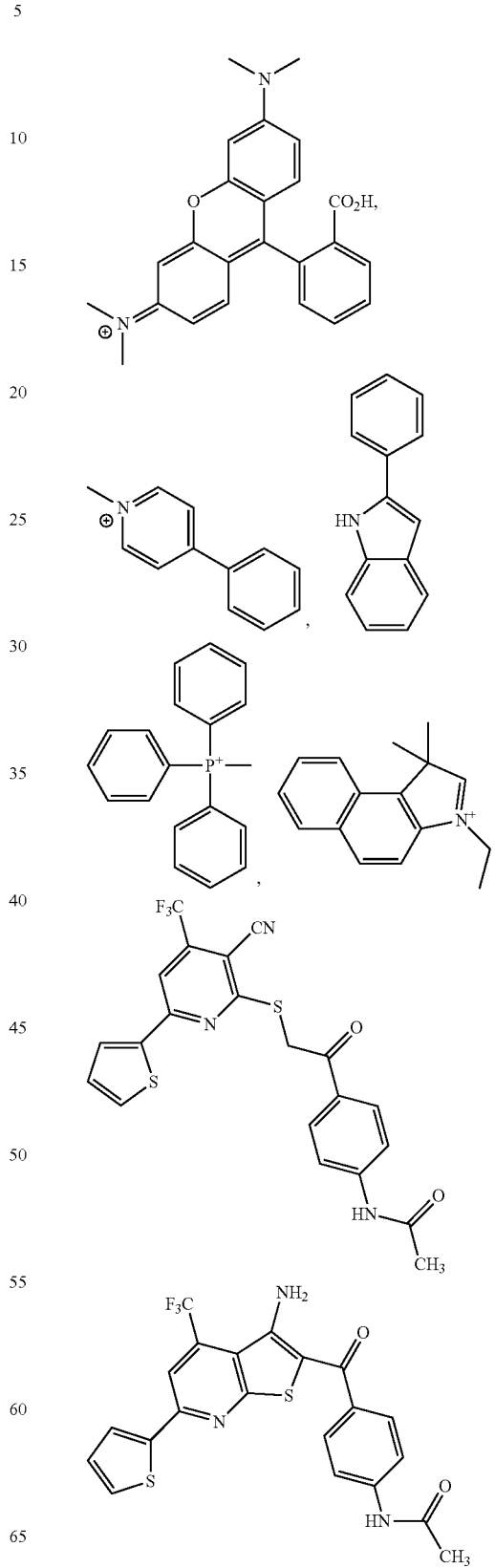

-continued

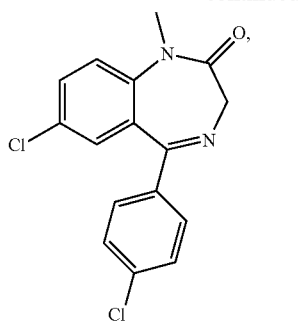

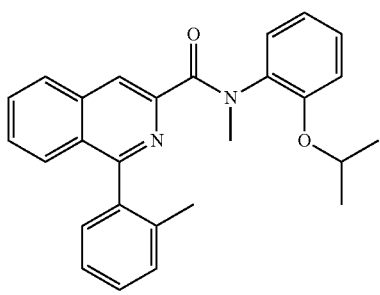

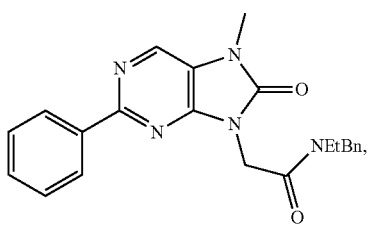

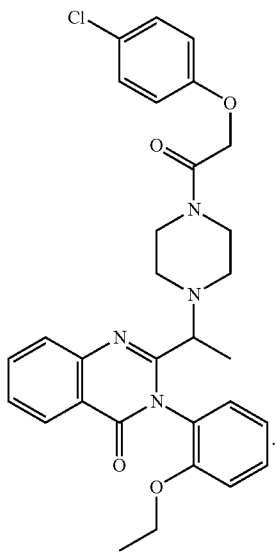

7. A pharmaceutical, comprising:
a compound or a salt thereof, the compound containing
  a ligand which binds to or accumulates in mitochondria,
  a substituent represented by the following general formula (1):

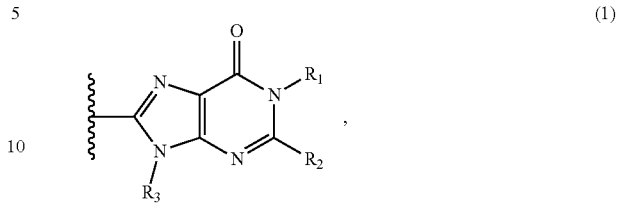

and
a linker, a first end of the linker being bound to the ligand and a second end of the linker being bound to the substitutent;
where $R^1$, $R^2$, and $R^3$ are identical to or different from each other,
wherein $R^1$ represents a hydrogen atom or a hydrocarbon group,
wherein $R^2$ represents a hydrogen atom, a hydrocarbon group that may be substituted, an amino group that may be substituted, or a carbamoyl group that may be substituted,
wherein $R^3$ represents a hydrogen atom or a hydrocarbon group that may be substituted,
wherein the pharmaceutical is effective to treat a disease that is treatable by degradation of injured mitochondria based on an autophagy mechanism, and
wherein the ligand is a protein comprising a mitochondrial targeting sequence.

8. A compound or the salt thereof, comprising:
a ligand which binds to or accumulates in mitochondria,
a substituent represented by the following general formula (1):

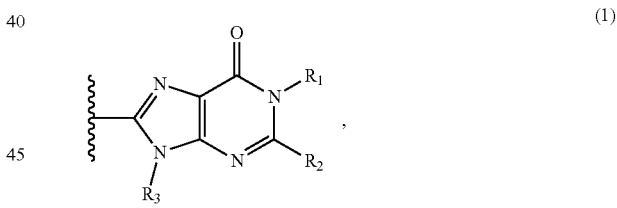

and
a linker, a first end of the linker being bound to the ligand and a second end of the linker being bound to the substitutent,
where $R^1$, $R^2$, and $R^3$ are identical to or different from each other,
wherein $R^1$ represents a hydrogen atom or a hydrocarbon group,
wherein $R^2$ represents a hydrogen atom, a hydrocarbon group that may be substituted, an amino group that may be substituted, or a carbamoyl group that may be substituted,
wherein $R^3$ represents a hydrogen atom or a hydrocarbon group that may be substituted,
wherein the pharmaceutical is effective to treat a disease that is treatable by degradation of injured mitochondria based on an autophagy mechanism, and
wherein the ligand is a protein comprising a mitochondrial targeting sequence.

9. A pharmaceutical comprising:
a compound or a salt thereof, the compound being represented by the following general formula (2):

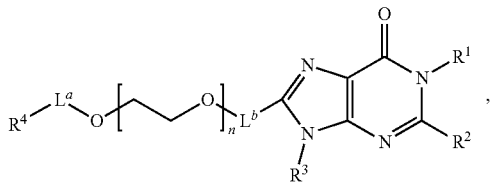
(2)

wherein $R^1$, $R^2$, and $R^3$ are identical to or different from each other,
wherein $R^1$ represents a hydrogen atom or a hydrocarbon group,
wherein $R^2$ represents a hydrogen atom, a hydrocarbon group that may be substituted, an amino group that may be substituted, or a carbamoyl group that may be substituted,
wherein $R^3$ represents a hydrogen atom or a hydrocarbon group that may be substituted,
wherein $R^4$ represents a ligand which binds to or accumulates on a mitochondrial surface,
wherein $L^a$ and $L^b$ are identical to or different from each other, and each represent a bond or a chain linker which has a main chain of 1 to 15 atoms and which may contain one or two divalent cyclic structure(s); and
wherein the main chain of the chain linker is formed of at least one kind selected from the group consisting of —$CH_2$—, —C(=O)—, —NH—, —O—, and —S—,
wherein the main chain of the chain linker contains at least one kind of structure selected from the group consisting of an amide bond [—C(=O)—NH— or —NH—C(=O)—] an ether bond (—O—),
a thioether bond (—S—) and one or two divalent cyclic structure(s),
wherein the main chain of the chain linker may be substituted,
wherein "n" represents a natural number of from 1 to 10 and
wherein the pharmaceutical is effective to treat a disease that is treatable by degradation of injured mitochondria based on an autophagy mechanism.

10. A compound or a salt thereof, the compound being represented by the following general formula (2):

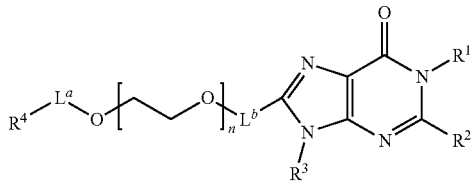
(2)

wherein $R^1$, $R^2$, and $R^3$ are identical to or different from each other,
wherein $R^1$ represents a hydrogen atom or a hydrocarbon group,
wherein $R^2$ represents a hydrogen atom, a hydrocarbon group that may be substituted, an amino group that may be substituted, or a carbamoyl group that may be substituted,
wherein $R^3$ represents a hydrogen atom or a hydrocarbon group that may be substituted,
wherein $R^4$ represents a ligand which binds to or accumulates on a mitochondrial surface,
wherein $L^a$ and $L^b$ are identical to or different from each other, and each represent a bond or a chain linker which has a main chain of 1 to 15 atoms and which may contain one or two divalent cyclic structure(s); and
wherein the main chain of the chain linker is formed of at least one kind selected from the group consisting of —$CH_2$—, —C(=O)—, —NH—, —O—, and —S—,
wherein the main chain of the chain linker contains at least one kind of structure selected from the group consisting of an amide bond [—C(=O)—NH— or —NH—C(=O)—], an ether bond (—O—),
a thioether bond (—S—) and one or two divalent cyclic structure(s), and one or two divalent cyclic structure(s),
wherein the main chain of the chain linker may be substituted,
wherein "n" represents a natural number of from 1 to 10 and
wherein the compound or the salt thereof inducing degradation of injured mitochondria based on an autophagy mechanism.

11. The pharmaceutical of claim 9, wherein the main chain comprises at least one kind of structure selected from the group consisting of —C(=O)—NH—, —NH—C(=O)—,

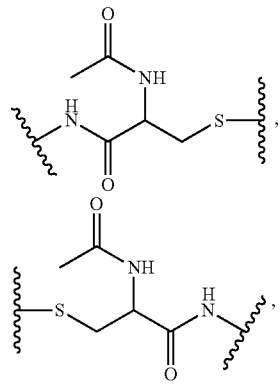

—C(=O)—C(=O)—NH—,
—NH—C(=O)—C(=O)—, —O—, and 1H-pyrazole-1,4-ylene.

12. The compound or salt thereof according to claim 10, wherein the main chain comprises at least one kind of structure selected from the group consisting of —C(=O)—NH—, —NH—C(=O)—,

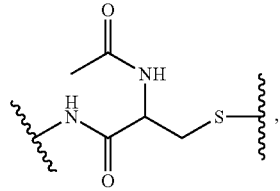

-continued

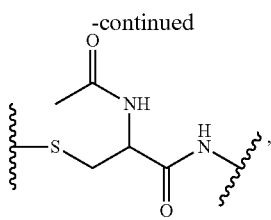

—C(=O)—C(=O)—NH—,
—NH—C(=O)—C(=O)—, —O—, and 1H-pyrazole-1,4-ylene.

13. The pharmaceutical of claim 9,
wherein the main chain comprises divalent cyclic structure(s),
wherein the divalent cyclic structure(s) are selected from following structures:

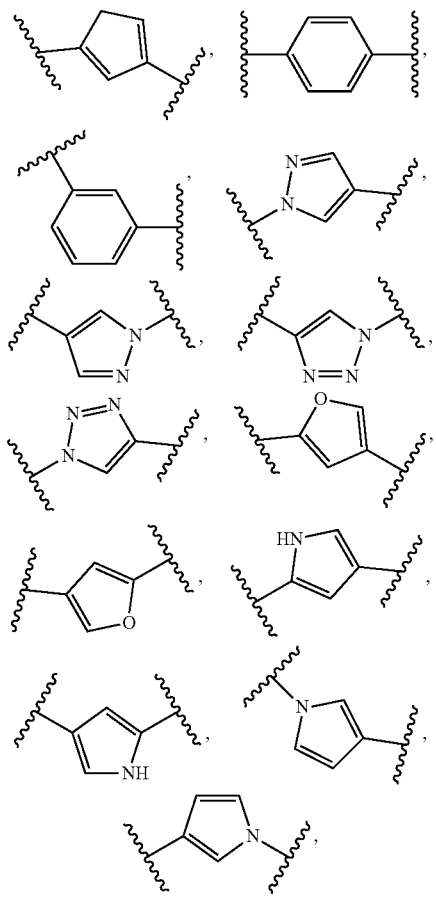

and wherein at least one hydrogen atom bonded to the unsaturated ring structure may be substituted.

14. The compound or salt thereof accoring to claim 10,
wherein the main chain comprises divalent cyclic structure(s),
wherein the divalent cyclic structure(s) are selected from following structures:

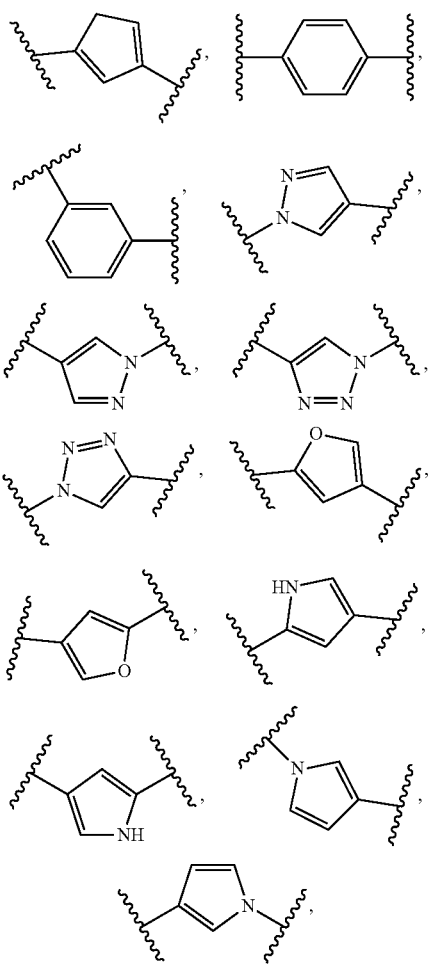

and wherein at least one hydrogen atom bonded to the unsaturated ring structure may be substituted.

* * * * *

SEQUENCE LISTING

```
<160> NUMBER OF SEQ ID NOS: 1

<210> SEQ ID NO 1
<211> LENGTH: 7386
<212> TYPE: DNA
<213> ORGANISM: Artificial Sequence
<220> FEATURE:
<223> OTHER INFORMATION: fusion peptide

<400> SEQUENCE: 1
tcaatattgg ccattagcca tattattcat tggttatata gcataaatca atattggcta        60
ttggccattg catacgttgt atctatatca taatatgtac atttatattg gctcatgtcc       120
aatatgaccg ccatgttggc attgattatt gactagttat taatagtaat caattacggg       180
gtcattagtt catagcccat atatggagtt ccgcgttaca taacttacgg taaatggccc       240
gcctggctga ccgcccaacg accccgccc attgacgtca ataatgacgt atgttcccat        300
agtaacgcca atagggactt tccattgacg tcaatgggtg gagtatttac ggtaaactgc       360
ccacttggca gtacatcaag tgtatcatat gccaagtccg cccctattg acgtcaatga        420 cggtaaatgg cccgcctggc attatgccca gtacatgacc ttacggact tcctacttg        480 gcagtacatc tacgtattag tcatcgctat taccatggtg atgcggtttt ggcagtacac       540
caatgggcgt ggatagcggt ttgactcacg ggatttcca agtctccacc ccattgacgt       600
caatgggagt ttgttttggc accaaaatca acgggacttt ccaaaatgtc gtaataaccc       660
```

-continued

```
cgccccgttg acgcaaatgg gcggtaggcg tgtacggtgg gaggtctata taagcagagc    720
tggtttagtg aaccgtcaga tcactagaag ctttattgcg gtagtttatc acagttaaat    780
tgctaacgca gtcagtgctt ctgacacaac agtctcgaac ttaagctgca gaagttggtc    840
gtgaggcact gggcaggtaa gtatcaaggt tacaagacag gtttaaggag accaatagaa    900
actgggcttg tcgagacaga gaagactctt gcgtttctga taggcaccta ttggtcttac    960
tgacatccac tttgcctttc tctccacagg tgtccactcc cagttcaatt acagctctta   1020
aggctagagt attaatacga ctcactatag ggctagcaaa gcgatcgctt ccgaattcat   1080
ggtgagcaag ggcgaggagc tgttcaccgg ggtggtgccc atcctggtcg agctggacgg   1140
cgacgtaaac ggccacaagt tcagcgtgtc cggcgagggc gagggcgatg ccacctacgg   1200
caagctgacc ctgaagttca tctgcaccac cggcaagctg cccgtgccct ggcccaccct   1260
cgtgaccacc ctgacctacg gcgtgcagtg cttcagccgc taccccgacc acatgaagca   1320
gcacgacttc ttcaagtccg ccatgcccga aggctacgtc caggagcgca ccatcttctt   1380
caaggacgac ggcaactaca agacccgcgc cgaggtgaag ttcgagggcg acaccctggt   1440
gaaccgcatc gagctgaagg gcatcgactt caaggaggac ggcaacatcc tggggcacaa   1500
gctggagtac aactacaaca gccacaacgt ctatatcatg gccgacaagc agaagaacgg   1560
catcaaggtg aacttcaaga tccgccacaa catcgaggac ggcagcgtgc agctcgccga   1620
ccactaccag cagaacaccc ccatcggcga cggccccgtg ctgctgcccg acaaccacta   1680
cctgagcacc cagtccgccc tgagcaaaga ccccaacgag aagcgcgatc acatggtcct   1740
gctggagttc gtgaccgccg ccgggatcac tctcggcatg gacgagctgt acaagtctag   1800
atttgggccc aattcctgca ggcgagctct cgagccaacc actgaggatc tgtactttca   1860
gagcgataac gatggatccg aaatcggtac tggctttcca ttcgaccccc attatgtgga   1920
agtcctgggc gagcgcatgc actacgtcga tgttggtccg cgcgatggca cccctgtgct   1980
gttcctgcac ggtaacccga cctcctccta cgtgtggcgc aacatcatcc cgcatgttgc   2040
accgacccat cgctgcattg ctccagacct gatcggtatg ggcaaatccg acaaaccaga   2100
cctgggttat ttcttcgacg accacgtccg cttcatggat gccttcatcg aagccctggg   2160
tctggaagag gtcgtcctgg tcattcacga ctggggctcc gctctgggtt tccactgggc   2220
caagcgcaat ccagagcgcg tcaaaggtat tgcatttatg gagttcatcc gccctatccc   2280
gacctgggac gaatggccag aatttgcccg cgagaccttc caggccttcc gcaccaccga   2340
cgtcggccgc aagctgatca tcgatcagaa cgttttttatc gagggtacgc tgccgatggg   2400
tgtcgtccgc ccgctgactg aagtcgagat ggaccattac cgcgagccgt tcctgaatcc   2460
tgttgaccgc gagccactgt ggcgcttccc aaaacgagctg ccaatcgccg gtgagccagc   2520
gaacatcgtc gcgctggtcg aagaatacat ggactggctg caccagtccc ctgtcccgaa   2580
gctgctgttc tggggcaccc caggcgttct gatcccaccg gccgaagccg ctcgcctggc   2640
caaaagcctg cctaactgca aggctgtgga catcggcccg ggtctgaatc tgctgcaaga   2700
agacaacccg gacctgatcg gcagcgagat cgcgcgctgg ctgtctactc tggagatttc   2760
cggtatgaac ggaagagtgg attatttggt cactgaggaa gagatcaatc ttaccagagg   2820
gccctcaggg ctgggcttca acatcgtcgg tgggacagat cagcagtatg tctccaacga   2880
cagtggcatc tacgtcagcc gcatcaaaga aaatggggct gcggccctgg atgggcggct   2940
ccaggagggt gataagatcc tttcggtaaa tggccaagac ctaaagaacc tgctgcacca   3000
ggatgctgta gacctctttc gtaatgcagg ctatgctgtg tctctgagag tgcagcacag   3060
```

```
ggtaggtatc actttgagcc agaaacctgg caccaggctt ttgcactgta cttctgaata    3120
agcccaatgt gtgtaatctt cagtgttgct ttttgtttta cttacaggtg cagaatggac    3180
ctataggaca tcgaggtgaa ggggacccaa gtggtattcc catatttatg gtgctggtgc    3240
cagtgtttgc cctcaccatg taatagaatt ggcatgcaag ctgatccggc tgctaacaaa    3300
gcccgaaagg aagctgagtt ggctgctgcc accgctgagc aataactagc ataacccctt    3360
ggggcggccg cttcgagcag acatgataag atacattgat gagtttggac aaaccacaac    3420
tagaatgcag tgaaaaaaat gctttatttg tgaaatttgt gatgctattg ctttatttgt    3480
aaccattata agctgcaata aacaagttaa caacaacaat tgcattcatt ttatgtttca    3540
ggttcagggg gagatgtggg aggttttttt aagcaagtaa aacctctaca aatgtggtaa    3600
aatcgaattt taacaaaata ttaacgctta caatttcctg atgcggtatt ttctccttac    3660
gcatctgtgc ggtatttcac accgcatacg cggatctgcg cagcaccatg cctgaaata    3720 acctctgaaa gaggaacttg gttaggtacc ttctgaggcg gaaagaacca gctgtggaat    3780
gtgtgtcagt tagggtgtgg aaagtcccca ggctccccag caggcagaag tatgcaaagc    3840
atgcatctca attagtcagc aaccaggtgt ggaaagtccc caggctcccc agcaggcaga    3900
agtatgcaaa gcatgcatct caattagtca gcaaccatag tcccgcccct aactccgccc    3960
atcccgcccc taactccgcc cagttccgcc cattctccgc cccatggctg actaattttt    4020
tttatttatg cagaggccga ggccgcctcg gcctctgagc tattccagaa gtagtgagga    4080
ggcttttttg gaggcctagg cttttgcaaa aagcttgatt cttctgacac aacagtctcg    4140
aacttaaggc tagagccacc atgattgaac aagatggatt gcacgcaggt tctccggccg    4200
cttgggtgga gaggctattc ggctatgact gggcacaaca gacaatcggc tgctctgatg    4260
ccgccgtgtt ccggctgtca gcgcaggggc gcccggttct ttttgtcaag accgacctgt    4320
ccggtgccct gaatgaactg caggacgagg cagcgcggct atcgtggctg gccacgacgg    4380
gcgttccttg cgcagctgtg ctcgacgttg tcactgaagc gggaagggac tggctgctat    4440
tgggcgaagt gccggggcag gatctcctgt catctcacct tgctcctgcc gagaaagtat    4500
ccatcatggc tgatgcaatg cggcggctgc atacgcttga tccggctacc tgcccattcg    4560
accaccaagc gaaacatcgc atcgagcgag cacgtactcg gatggaagcc ggtcttgtcg    4620
atcaggatga tctggacgaa gagcatcagg ggctcgcgcc agccgaactg ttcgccaggc    4680
tcaaggcgcg catgcccgac ggcgaggatc tcgtcgtgac ccatggcgat gcctgcttgc    4740
cgaatatcat ggtggaaaat ggccgctttt ctggattcat cgactgtggc cggctgggtg    4800
tggcggaccg ctatcaggac atagcgttgg ctacccgtga tattgctgaa gagcttggcg    4860
gcgaatgggc tgaccgcttc ctcgtgcttt acggtatcgc cgctcccgat tcgcagcgca    4920
tcgccttcta tcgccttctt gacgagttct tctgagcggg actctggggt tcgaaatgac    4980
cgaccaagcg acgcccaacc tgccatcacg atggccgcaa taaaatatct ttattttcat    5040
tacatctgtg tgttggtttt tgtgtgaat cgatagcgat aaggatcctc tttgcgcttg    5100
cgttttccct tgtccagata gcccagtagc tgacattcat ccggggtcag caccgtttct    5160
gcggactggc tttctacgta atggtttctt agacgtcagg tggcactttt cggggaaatg    5220
tgcgcggaac ccctatttgt ttatttttct aaatacattc aaatatgtat ccgctcatga    5280
gacaataacc ctgataaatg cttcaataat attgaaaaag gaagagtatg agtattcaac    5340
atttccgtgt cgcccttatt ccctttttg cggcattttg ccttcctgtt tttgctcacc    5400
```

-continued

| | |
|---|---|
| cagaaacgct ggtgaaagta aaagatgctg aagatcagtt gggtgcacga gtgggttaca | 5460 |
| tcgaactgga tctcaacagc ggtaagatcc ttgagagttt tcgccccgaa gaacgttttc | 5520 |
| caatgatgag cactttcaaa gttctgctat gtggcgcggt attatcccgt attgacgccg | 5580 |
| ggcaagagca actcggtcgc cgcatacact attctcagaa tgacttggtt gagtactcac | 5640 |
| cagtcacaga aaagcatctt acggatggca tgacagtaag agaattatgc agtgctgcca | 5700 |
| taaccatgag tgataacact gcggccaact tacttctgac aactatcgga ggaccgaagg | 5760 |
| agctaaccgc ttttttgcac aacatggggg atcatgtaac tcgccttgat cgttgggaac | 5820 |
| cggagctgaa tgaagccata ccaaacgacg agcgtgacac cacgatgcct gtagcaatgg | 5880 |
| caacaacgtt gcgcaaacta ttaactggcg aactacttac tctagcttcc cggcaacaat | 5940 |
| taatagactg gatggaggcg gataaagttg caggaccact tctgcgctcg gcccttccgg | 6000 |
| ctggctggtt tattgctgat aaatctggag ccggtgagcg tgggtctcgc ggtatcattg | 6060 |
| cagcactggg gccagatggt aagccctccc gtatcgtagt tatctacacg acggggagtc | 6120 |
| aggcaactat ggatgaacga atagacaga tcgctgagat aggtgcctca ctgattaagc | 6180 |
| attggtaatt cgaaatgacc gaccaagcga cgcccaaccg gtatcagctc actcaaaggc | 6240 |
| ggtaatacgg ttatccacag aatcagggga taacgcagga agaacatgt gagcaaaagg | 6300 |
| ccagcaaaag gccaggaacc gtaaaaaggc cgcgttgctg gcgttttttcc ataggctccg | 6360 |
| cccccctgac gagcatcaca aaaatcgacg ctcaagtcag aggtggcgaa acccgacagg | 6420 |
| actataaaga taccaggcgt ttccccctgg aagctccctc gtgcgctctc ctgttccgac | 6480 |
| cctgccgctt accggatacc tgtccgcctt tctcccttcg ggaagcgtgg cgctttctca | 6540 |
| tagctcacgc tgtaggtatc tcagttcggt gtaggtcgtt cgctccaagc tgggctgtgt | 6600 |
| gcacgaaccc cccgttcagc ccgaccgctg cgccttatcc ggtaactatc gtcttgagtc | 6660 |
| caacccggta agacacgact tatcgccact ggcagcagcc actggtaaca ggattagcag | 6720 |
| agcgaggtat gtaggcggtg ctacagagtt cttgaagtgg tggcctaact acggctacac | 6780 |
| tagaaggaca gtatttggta tctgcgctct gctgaagcca gttaccttcg gaaaaagagt | 6840 |
| tggtagctct tgatccggca aacaaaccac cgctggtagc ggtggttttt tgtttgcaa | 6900 |
| gcagcagatt acgcgcagaa aaaaaggatt caagaagat cctttgatct tttctacggg | 6960 |
| gtctgacgct cagtggaacg aaaactcacg ttaagggatt ttggtcatga gattatcaaa | 7020 |
| aaggatcttc acctagatcc ttttatagtc cggaaataca ggaacgcacg ctggatggcc | 7080 |
| cttcgctggg atggtgaaac catgaaaaat ggcagcttca gtggattaag tgggggtaat | 7140 |
| gtggcctgta ccctctggtt gcataggtat tcatacggtt aaaatttatc aggcgcgatt | 7200 |
| gcggcagttt ttcgggtggt ttgttgccat ttttacctgt ctgctgccgt gatcgcgctg | 7260 |
| aacgcgtttt agcggtgcgt acaattaagg gattatggta aatccactta ctgtctgccc | 7320 |
| tcgtagccat cgagataaac cgcagtactc cggccacgat gcgtccggcg tagaggatcg | 7380 |
| agatct | 7386 |